United States Patent
Reiter et al.

(10) Patent No.: US 7,129,053 B1
(45) Date of Patent: Oct. 31, 2006

(54) IMMUNO-CHROMATOGRAPHIC RAPID ASSAY IN ORDER TO DETECT ACID-RESISTANT MICROORGANISMS IN THE STOOL

(75) Inventors: Christian Reiter, Martinsried (DE); Gerhard Cullman, München (DE); Meret Lakner, München (DE); Andreas Trüe, Pasing (DE); Sonja Dehnert, München (DE); Georg Schwartz, München (DE)

(73) Assignee: Dakocytomation Denmark A/S (DE)

( * ) Notice: Subject to any disclaimer, the term of this patent is extended or adjusted under 35 U.S.C. 154(b) by 0 days.

(21) Appl. No.: 10/110,410

(22) PCT Filed: Oct. 12, 2000

(86) PCT No.: PCT/EP00/10057

§ 371 (c)(1),
(2), (4) Date: Oct. 22, 2003

(87) PCT Pub. No.: WO01/27612

PCT Pub. Date: Apr. 19, 2001

(30) Foreign Application Priority Data

| Oct. 12, 1999 | (EP) | ................................. 99120351 |
| Mar. 16, 2000 | (EP) | ................................. 00105592 |
| Mar. 31, 2000 | (EP) | ................................. 00107028 |
| May 10, 2000 | (EP) | ................................. 00110110 |

(51) Int. Cl.
  G01N 1/30 (2006.01)
  G01N 33/53 (2006.01)
  G01N 33/567 (2006.01)
  G01N 33/569 (2006.01)
(52) U.S. Cl. .................... 435/7.1; 435/7.2; 435/7.31; 435/40.5; 435/975
(58) Field of Classification Search ............... 435/7.1, 435/7.2, 7.31, 40.5, 975
See application file for complete search history.

(56) References Cited

U.S. PATENT DOCUMENTS

| 5,712,170 A | 1/1998 | Kouvonen et al. |
| 5,932,430 A | 8/1999 | Larka et al. |

FOREIGN PATENT DOCUMENTS

| EP | 0291194 | 4/1988 |
| EP | 0 806 667 B1 | 2/2002 |
| WO | 0044066 | 9/1999 |
| WO | 0026671 | 5/2000 |

OTHER PUBLICATIONS

Trevisani, L. et al. 1999. Evaluation of a new enzyme immunoassay for detecting *Helicobacter pylori* in feces: A prospective pilot study. Am J. Gastroenterol. 94(7): 1830-1833.*

*H. pylori* Stool Antigen Test Medical Information; Web page of Meridian Bioscience: HpSA *Heycobacter pylori* Stool Antigen—Medical Information (Website: WWW.MDEUR.COM), May 5, 2004.

*Journal of Clinical Microbiology*, vol. 36, No. 10, pp. 2803-2809, (1998) . Laheij et al., "Evaluation of Commercially Available *Helicobactor pylori* Serology Kits: a Review."

* cited by examiner

Primary Examiner—Mark Navarro
(74) Attorney, Agent, or Firm—Nixon Peabody LLP; Jeffrey A. Lindeman

(57) ABSTRACT

The invention relates to a method for detecting an infection of a mammal with an acid-resistant microorganism comprising the following steps: (a) provision of an immunochromatographic test with a sample application area for the application of a stool sample of the mammal with an antigen and application of the stool sample, (b) incubation of the stool sample using (i) a first receptor under conditions permitting a complex formation of the antigen from the acid resistant microorganism with the receptor; or (ii) at least two different first receptors under conditions permitting a complex formation of the antigen from the acid-resistant microorganism with the at least two first receptors and wherein the first receptor according to (i) or the first receptors according to (ii) specifically bind(s) an antigen which shows, at least with some mammals, a structure after passage through the intestine that corresponds to the native structure or the structure against which a mammal produces antibodies against after being infected or immunized with the acid-resistant microorganism or an extract or lysate thereof or a protein therefrom or a fragment thereof or a synthetic peptide produces antibodies; and (c) provision of a second receptor immobilized at an analysis region, wherein the second receptor binds an antigen receptor complex according to (b) and (d) transport and detection of the formation of at least one antigen receptor complex according to (b) by accumulation of the antigen receptor complex at the second receptor in the analysis area. The invention further relates to an immunochromatographic test which is particularly suitable and designed to carry out the method of the invention.

60 Claims, 9 Drawing Sheets

Fig. 1

Figure 9:
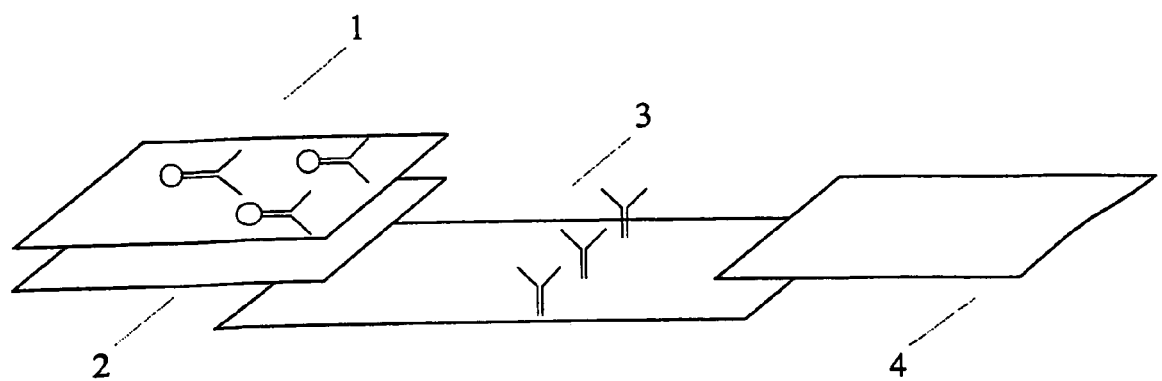

| | | | | | | | | | |
|---|---|---|---|---|---|---|---|---|---|
|+1|E|V|Q|L|L|E|Q|P|G|A|

GAGGTGCAGCTGCTCGAGCAGCCTGGGGCT 30

+1    E    L    A    K    P    G    A    S    V    K
GAACTGGCAAAACCTGGGGCCTCAGTGAAG 60

+1    M    S    C    K    A    S    G    Y    T    F
ATGTCCTGCAAGGCTTCTGGCTACACCTTT 90

+1    T    N    Y    W    I    H    W    V    K    Q
ACT<u>AACTACTGGATTCAC</u>TGGGTGAAACAG 120

+1    R    P    G    Q    G    L    K    W    I    G
AGGCCTGGACAGGGTCTGAAATGGATTGGA 150

+1    Y    I    N    P    A    T    G    S    T    S
<u>TACATTAATCCTGCCACTGGTTCCACTTCT</u> 180

+1    Y    N    Q    D    F    Q    D    R    A    T
<u>TACAATCAGGACTTTCAGGA</u>CAGGGCCACT 210

+1    L    T    A    D    K    S    S    T    T    A
TTGACCGCAGACAAGTCCTCCACCACAGCC 240

+1    Y    M    Q    L    T    S    L    T    S    E
TACATGCAGCTGACCAGCCTGACATCTGAG 270

+1    D    S    S    V    Y    Y    C    A    R    E
GACTCTTCAGTCTATTACTGTGCAAGA<u>GAG</u> 300

+1    G    Y    D    G    F    D    S    W    G    Q
<u>GGGTACGACGGGTTTGACTCC</u>TGGGGCCAA 330

+1    G    T    T    L    T    V    S    S
GGCACCACTCTCACAGTCTCCTCA 360

Fig. 2

```
+1   E   L   V   L   T   Q   S   P   A   I
     GAGCTCGTGCTCACCCAGTCTCCAGCAATC           30

+1   M   S   A   S   P   G   E   K   V   T
     ATGTCTGCATCTCCAGGGGAGAAGGTCACC           60

+1   M   T   C   S   A   S   S   S   V   N
     ATGACCTGCAGTGCCAGCTCAAGTGTAAAT           90

+1   Y   M   Y   W   Y   Q   Q   K   S   G
     TACATGTACTGGTACCAGCAGAAGTCAGGC          120

+1   T   S   P   K   R   W   I   Y   D   T
     ACCTCCCCCAAAAGATGGATTTATGACACA          150

+1   S   K   L   A   S   G   V   P   A   R
     TCCAAATTGGCTTCTGGAGTCCCTGCTCGC          180

+1   F   S   G   S   G   S   G   T   S   Y
     TTCAGTGGCAGTGGGTCTGGGACCTCTTAC          210

+1   S   L   T   L   S   S   M   E   A   E
     TCTCTCACACTCAGCAGCATGGAGGCTGAA          240

+1   D   A   A   T   Y   Y   C   Q   Q   W
     GATGCCGCCACTTATTACTGCCAGCAGTGG          270

+1   S   S   N   P   Y   T   F   G   G   G
     AGTAGTAATCCGTACACGTTCGGAGGGGGG          300

+1   T   K   L   E   I   K
     ACCAAGCTGGAGATAAAA                      330
```

Fig. 3

| | | | | | | | | | | |
|---|---|---|---|---|---|---|---|---|---|---|
| +1 | E | V | Q | L | Q | Q | S | G | A | E |
| | GAGGTTCAGCTGCAGCAGTCTGGGGCAGAG | | | | | | | | | 30 |
| +1 | L | V | K | P | G | A | S | V | K | L |
| | CTTGTGAAGCCTGGGGCCTCAGTCAAGTTG | | | | | | | | | 60 |
| +1 | S | C | T | S | S | G | F | N | I | K |
| | TCCTGCACATCTTCTGGCTTCAACATTAAA | | | | | | | | | 90 |
| +1 | D | T | Y | V | H | W | M | K | Q | R |
| | <u>GACACCTATGTGCAC</u>TGGATGAAACAGAGG | | | | | | | | | 120 |
| +1 | P | E | Q | G | L | E | W | I | G | K |
| | CCTGAACAGGGCCTGGAGTGGATTGGA<u>AAG</u> | | | | | | | | | 150 |
| +1 | I | D | P | A | N | G | K | T | K | Y |
| | <u>ATTGATCCTGCAATGGTAAAACTAAATAT</u> | | | | | | | | | 180 |
| +1 | D | P | I | F | Q | A | K | A | T | M |
| | <u>GACCCGATATTCCAGGC</u>AAGGCCACTATG | | | | | | | | | 210 |
| +1 | T | A | D | A | S | S | N | T | A | Y |
| | ACAGCAGACGCATCCTCCAATACAGCCTAC | | | | | | | | | 240 |
| +1 | L | Q | L | S | S | L | T | S | E | D |
| | CTGCAACTCAGCAGCCTGACTTCTGAGGAC | | | | | | | | | 270 |
| +1 | T | A | V | Y | Y | C | A | L | P | I |
| | ACTGCCGTCTATTACTGTGCTCT<u>CCCATT</u> | | | | | | | | | 300 |
| +1 | Y | Y | A | S | S | W | F | A | Y | W |
| | <u>TATTACGCTAGTTCCTGGTTTGCTTACTGG</u> | | | | | | | | | 330 |
| +1 | G | Q | G | T | L | V | T | V | S | A |
| | GGCCAAGGGACTCTGGTCACTGTCTCTGCA | | | | | | | | | 360 |

Fig. 4

| | | | | | | | | | |
|---|---|---|---|---|---|---|---|---|---|
|+1|D|I|V|M|T|Q|S|H|K|F|

GACATTGTGATGACCCAGTCTCACAAATTC 30

+1 M S T S V G D R V S

ATGTCCACATCAGTAGGAGACAGGGTCAGC 60

+1 I T C K A S Q D V G

ATCACCTGCAAGGCCAGTCAGGATGTGGGT 90

+1 T S V A W Y Q Q K P

ACTTCTGTTGCCTGGTATCAACAGAAACCT 120

+1 G H S P K L L I Y W

GGGCACTCTCCTAAATTACTGATTTACTGG 150

+1 T S T R H T G V P D

ACATCCACCCGGCACACTGGAGTCCCTGAT 180

+1 R F T G S G S G T D

CGCTTCACAGGCAGTGGATCTGGACAGAT 210

+1 F I L T I S N V Q S

TTCATTCTCACCATTAGCAATGTGCAGTCT 240

+1 E D L A D Y F C Q Q

GAAGACTTGGCAGATTATTTCTGTCAGCAA 270

+1 Y S S S P T F G G G

TATAGCAGCTCTCCACGTTCGGAGGGGGG 300

+1 A K V E I K

GCCAAGGTGGAAATAAAA 330

Fig. 5

```
+1   D    I    L    L    T    Q    S    P    A    I    L    S    V    S    P    G    E

GACATCTTGC TGACTCAGTC TCCAGCCATC CTGTCTGTGA GTCCAGGAGA  50
+1     R    V    S    F    S    C    R    A    S    Q    S    I    G    T    R    I    H

AAGAGTCAGT TTCTCCTGCA GGGCCAGTCA GAGCATTGGC ACAAGAATAC  100
+1     W    Y    Q    Q    R    T    N    G    S    P    R    L    L    I    K    Y

ACTGGTATCA ACAAAGAACA AATGGTTCTC CAAGGCTTCT CATAAAGTAT  150
+1    G    S    E    S    I    S    G    I    P    S    R    F    S    G    S    G    S

GGTTCTGAGT CTATCTCTGG GATCCCTTCC AGGTTTAGTG GCAGTGGATC  200
+1     G    T    D    F    S    L    S    I    N    S    V    E    S    E    D    I    A

AGGGACAGAT TTTAGTCTTA GCATCAACAG TGTCGAGTCT GAAGATATTG  250
+1     D    Y    Y    C    Q    Q    S    N    T    W    P    L    T    F    G    A

CAGATTATTA CTGTCAACAA AGTAATACCT GGCCGCTCAC GTTCGGTGCT  300
+1     G    T    K    L    E    L    K

GGGACCAAGC TGGAGCTGAA A                                  350
```

Fig. 6

```
+1  E   V   Q   L   L   E   Q   S   G   A   E   L   V   K   P   G   A

GAGGTGCAGC TGCTCGAGCA GTCTGGAGCT GAGCTGGTGA AGCCTGGGGC  50

+1  S   V   K   I   S   C   K   A   S   G   Y   A   F   S   T   S   W

CTCAGTGAAG ATTTCCTGCA AGGCTTCTGG CTACGCATTC AGTACCTCCT  100

+1  M   N   W   V   K   Q   R   P   G   K   G   L   E   W   I   G

GGATGAACTG GGTGAAACAG AGGCCTGGAA AGGGTCTTGA GTGGATTGGA  150

+1  R   I   Y   P   G   D   G   D   T   N   Y   N   G   K   F   K   G

CGGATTTATC CTGGAGATGG AGATACTAAC TACAATGGGA AGTTCAAGGG  200

+1  K   A   T   L   T   A   Q   K   S   S   S   T   A   Y   M   Q   L

CAAGGCCACA CTGACTGCAG ACAAATCCTC CAGCACAGCC TACATGCAAC  250

+1  N   S   L   T   S   E   D   S   A   V   Y   F   C   V   R   E

TCAACAGCCT GACATCTGAG GACTCTGCGG TCTACTTCTG TGTAAGAGAG  300

+1  D   A   Y   Y   S   N   P   Y   S   L   D   Y   W   G   Q   G   T

GATGCCTATT ATAGTAACCC CTATAGTTTG GACTACTGGG GTCAAGGAAC  350

+1  S   V   T   V   S   S

CTCAGTCACC GTCTCCTCA                                    400
```

Fig. 7

```
+1   E   L   Q   M   T   Q   S   P   S   S   L   S   A   S   L   G   D

GAGCTCCAGA TGACCCAGTC TCCATCCAGT CTGTCTGCAT CCCTTGGAGA   50
+1   T   I   T   I   T   C   H   A   S   Q   N   I   N   V   W   L   S

CACAATTACC ATCACTTGCC ATGCCAGTCA GAACATTAAT GTTTGGTTAA  100
+1   W   Y   Q   Q   K   P   G   D   I   P   K   L   L   I   Y   K

GCTGGTATCA GCAGAAACCA GGAGATATCC CTAAACTATT GATCTATAAG  150
+1   A   S   N   L   H   T   G   V   P   S   R   F   S   G   S   G   S

GCTTCCAACT TGCACACAGG CGTCCCATCA AGGTTTAGTG GCAGTGGATC  200
+1   G   T   G   F   T   L   V   I   S   S   L   Q   P   E   D   I   A

TGGAACAGGT TTCACATTAG TCATCAGCAG CCTGCAGCCT GAAGACATTG  250
+1   T   Y   Y   C   Q   Q   G   R   S   Y   P   L   T   F   G   A

CCACTTACTA CTGTCAACAG GGTCGAAGTT ATCCTCTCAC GTTCGGTGCT  300
+1   G   T   K   L   E   L   K

GGGACCAAGC TGGAGCTGAA A                                  350
```

Fig. 8

```
+1   E    V    Q    L    L    E    E    S    G    G    G    L    V    K    P    G    G

GAGGTGCAGC TGCTCGAGGA GTCTGGGGGA GGCTTAGTGA AGCCTGGAGG  50
+1   S    L    Q    L    S    C    S    A    S    G    F    T    F    S    S    H    F

GTCCCTGCAA CTCTCCTGTT CAGCCTCTGG ATTCACTTTC AGTAGCCATT 100
+1   M    S    W    V    R    Q    T    P    E    K    R    L    E    W    V    A

TCATGTCTTG GGTTCGCCAA ACTCCAGAGA AGAGGCTGGA GTGGGTCGCA 150
+1   S    I    S    S    G    G    D    S    F    Y    P    D    S    L    K    G    R

TCCATTAGTA GTGGTGGTGA CAGTTTCTAT CCAGACAGTC TGAAGGGCCG 200
+1   F    A    I    S    R    D    N    A    R    N    I    L    F    L    Q    M    S

ATTCGCCATC TCCAGAGATA ATGCCAGGAA CATCCTGTTC CTGCAAATGA 250
+1   S    L    R    S    E    D    S    A    M    Y    F    C    T    R    D    Y

GCAGTCTGAG GTCTGAGGAC TCGGCCATGT ATTTCTGTAC AAGAGACTAC 300
+1   S    W    Y    A    L    D    Y    W    G    Q    G    T    S    V    T    V    S

TCTTGGTATG CTTTGGACTA CTGGGGTCAA GGAACCTCAG TCACCGTCTC 350
+1   S

CTCA                                                  400
```

IMMUNO-CHROMATOGRAPHIC RAPID ASSAY IN ORDER TO DETECT ACID-RESISTANT MICROORGANISMS IN THE STOOL

The description of this invention mentions a number of published documents. The subject matter of these documents is herewith incorporated into the specification by reference.

The invention relates to an immunochromatographic rapid test, in particular, a test strip for detecting an infection of a mammal with an acid-resistant microorganism, wherein (a) a stool sample of the mammal is incubated with (aa) a receptor under conditions permitting a complex formation of an analyte or antigen from the acid resistant microorganism with the receptor; or (ab) at least two different receptors under conditions permitting a complex formation of an analyte or antigen of the acid-resistant microorganism with the at least two receptors and wherein the receptor according to (aa) or the receptors according to (ab) specifically bind(s) an analyte or antigen which shows, at least with some mammals, a structure after passage through the intestine that corresponds to the native structure or the structure which a mammal produces antibodies against after being infected or immunized with the acid-resistant microorganism or an extract or lysate thereof or a protein therefrom or a fragment thereof or a synthetic peptide; and (b) wherein the formation of at least one antigen- or analyte-receptor complex according to (a) is detected. Preferably, the acid-resistant microorganism is a bacterium, in particular *Helicobacter pylori*, *Helicobacter hepaticus*, *Campylobacter jejuni* or *Mycobacterium tuberculosis*. Moreover, the receptor(s) preferably bind(s) to (an) epitope(s) of a catalase, urease or metalloproteinase. Furthermore, the invention relates to diagnostic and pharmaceutical compositions and test devices containing said components and packaging containing the same.

Today, there are various invasive, semi-invasive or non-invasive methods for detecting the infection of a mammalian organism with a microbial pathogen or parasite. All invasive methods presuppose endoscopy and biopsy. If these techniques are used, the physical integrity of the examined subject is violated, e.g. in a biopsy. Obtaining a specimen by biopsy is time-consuming, costly and mostly puts a strain on the patient. As the infection with particular microorganisms, for instance with *H. pylori*, need not be distributed over the entire gastric mucosa, obtaining a specimen by biopsy at a non-infected site may deliver a false-negative result. Another disadvantage of all invasive methods is that all examination results are influenced by an earlier treatment with proton-pump inhibitors, bismuth or antibiotics.

Semi-invasive or non-invasive diagnostic methods note changes in parameters which may be measured without interfering in the organism. For this purpose preferably samples of body fluids and excretions, such as serum, breath, urine, saliva, sweat or stool are taken and analysed.

Due to the detected parameters, diagnostic methods can be divided into direct and indirect methods. With direct methods the presence of the pathogen or parasite, its components or their degradation products is detected by electron microscopy, optical characterization, mass spectrometry, measurement of the radioactive degradation products or specific enzymatic reactions. However, these methods often require expensive and sophisticated instruments (e.g. the breath test). By contrast, indirect methods are used for detecting reactions of the host organism to the pathogen or the parasite, for instance the presence of antibodies against antigens of the pathogen in the serum or the saliva of the host.

Since interfering in the organism using invasive techniques strains the organism in most cases and also requires expensive and sophisticated instruments and involves health hazards, non-invasive techniques are the methods of choice since it is comparatively simple to take samples of the above-mentioned body fluids and excretions. Furthermore, since not every host reacts in the same way to a particular pathogen or parasite, and the host's reaction is delayed and may persist even after the pathogen or parasite has been removed from the organism, direct methods should always be preferred. Hence, ideally, a diagnosis is made by means of the non-invasive, direction detection of the pathogen or parasite in body fluids or excretions. Contrary to indirect methods, this allows the current infection status to be determined.

Moreover, a diagnostic method should also be optimised with regard to other aspects: high reproducibility, sensitivity and specificity, guaranteed availability and constant quality of the materials to be used, low costs for producing and carrying out the method and simple application independent of expensive and sophisticated instruments are parameters to be taken into consideration.

For the above-mentioned reasons, in medical diagnostics increasing use is made of methods based on the high selectivity and binding affinity of particular classes of substances (e.g. antibodies, receptors, lectins, aptamers) for molecular structures which can be selected in such a way that they are highly specific for the corresponding substance to be analysed. It was mainly the possibility of immobilizing these substances on the surface of solids as well as the coupling of radioactive nuclides, of enzymes triggering colour reactions with suitable substrates or of coloured particles with a highly specific binding affinity (e.g. ELISA=enzyme-linked immunosorbent assay) that led to the development of inexpensive, simple and less timely methods for detecting substances that are naturally-occurring in the body or foreign to body.

In the initial phases of the development of these detection methods exclusively polyclonal antibodies were used. They, however, have several disadvantages well known to the person skilled in the art, chief among these are limited availability and often cross-reactivity. The development of methods for preparing monoclonal antibodies (Köhler & Milstein (1975)), the advances in the isolation of receptors and their directed expression in cellular host systems, the development of lectins with high affinity to particular carbohydrates and the discovery that single-stranded nucleic acid molecules (aptamers) are able to specifically bind molecular structures, allowed the majority of these disadvantages to be eliminated. Today, the specificity and sensitivity of detection methods can be optimised with comparatively simple methods.

Due to the high specificity, such methods are particularly suitable for detecting individual, defined substances such as haptens, peptides or proteins, provided the structural element that has been recognised is constant within the specimen population to be examined and specific to the substance to be detected. Moreover, they are well suited for measurements in body fluids and, thus, are an obvious option for the direct detection of pathogens in this specimen matrix. Accordingly, the prior art describes methods for diagnosing e.g. *Entamoeba histolytica* (Hague (1993), J. Infect. Dis. 167: 247–9), enterohemorrhagic *Escherichia coli* (EHEC, Park (1996), J. Clin. Microbiol. 34: 988–990), *Vibrio chol-*

*erae* (Hasan (1994), FEMS Microbiol. Lett. 120: 143–148), Toro virus-like particles (Koopmans (1993) J. Clin. Microbiol. 31: 2738–2744) or *Taenia saginata* (Machnicka (1996), Appl. Parasitol. 37: 106–110) from stool.

The feature the above-described pathogens have in common is that they are viable and reproducible in the intestine of the host, in all cases humans. Hence, they have mechanisms allowing them to survive and propagate in the presence of the degradation and digestion systems active in the intestine. Thus, a large number of intact or almost intact pathogens or parasites are likely to be passed with the stool. As a rule, it is easy to detect them in the stool or in prepared stool samples by means of detection reagents, for instance antibodies that recognise the intact pathogens or parasites.

There is, however, a number of pathogens or parasites that, on the one hand, may be present in the stool due to the relations of the affected tissue (e.g. lungs, stomach, pancreas, duodenum, liver) to the gastrointestinal tract and that, on the other hand, are not viable and/or reproducible in the intestine itself. These pathogens and parasites include, for instance, *Helicobacter pylori* (*H. pylori*) and *Helicobacter hepatis, Mycobacterium tuberculosis* and other mycobacteria, *Chlamydia pneumoniae, Legionella pneumophilae, Pneumocystis carinii* and others.

Other pathogens, such as *Legionella pneumophilae* can be detected specifically by means of antigens which get into the urine via the kidneys. Yet, this is only possible if the amount present in the urine is sufficient for the detection. Detection in the stool would be a good alternative. In these organisms, however, passage through the intestine is combined with a strong attack by the digestion and degradation mechanisms of the intestinal flora. In this case, molecular structures which are specific to the pathogen observed can be destroyed or their concentration can be greatly reduced.

With acid-resistant bacteria too, the degradation of pathogens in the intestine has turned out to be a problem for reliable detection in stool samples. The number of germs in the stomach of an infected patient is small compared to the number of other bacteria settling in the intestine. Furthermore, germs and germ fragments have to pass a long way through the intestine, which is rich in proteases, after leaving the stomach. Due to these circumstances, only small amounts of intact proteins can be found in the stool. It can, however, not be assumed that always the same fragment of specific proteins pass the intestinal tract undamaged. Another consequence of this is that the combination of two epitopes on one antigen, which is necessary for ELISA or an immunochromatographic rapid test, is no longer necessarily like the one occurring in the native protein and epitopes located closely to each other are most likely to show a positive result in a detection method requiring two epitopes on the same molecule. Ideally, only one epitope on the same molecule is needed for detection, wherein this epitope, in the case of a monomer, has to be present twice on said molecule. In the case of a dimer, it would be sufficient if the epitope was present once on each subunit. In addition, the distribution of antigens detected in the stool of infected patients, which may differ individually, suggests individual features in the processing of the antigens during passage through the intestine. A first approach to reduce this problem has been provided by the disclosure of EP-A 0 806 667. In this application it was shown that polyclonal antibodies could be induced with the lysate of a particular *H. pylori* strain. These antibodies recognize a greater variability of strains from different geographical regions. However, this application does not indicate which antigens are recognized by the serum. In view of the fact that immune sera may vary in spite of all standardisation efforts, the method developed in the above-mentioned application must be regarded as suboptimal for broad application. In addition, it is necessary to keep immunizing new animals in order to provide polyclonal sera. The corresponding methods are both time-consuming and costly.

Ideally, a single or a limited number of reagent(s) specific to this pathogenic organism/parasite should enable the reliable detection of the infection of an acid-resistant pathogenic organism/parasite as broadened above.

EP 201 194 describes an analytical test device containing a porous carrier with a specific binding reagent, mobile in moist condition, for an analyte and a permanently immobilized, unmarked specific binding reagent for the same analyte.

Hence, the technical problem underlying the present invention is to provide a corresponding simple and cost-efficient test.

This technical problem has been solved by providing the embodiments characterized in the claims.

Thus, the invention relates to a method for detecting an infection of a mammal with an acid-resistant microorganism, wherein (a) a stool sample of the mammal is incubated with (aa) a receptor under conditions permitting the formation of a complex of an antigen from the acid-resistant microorganism with the receptor; or (ab) at least two different receptors under conditions permitting the formation of a complex of an antigen from the acid-resistant microorganism with the at least two receptors, and wherein the receptor according to (aa) or the receptors according to (ab) specifically bind(s) to an antigen which shows, at least with some mammals, a structure after passage through the intestine that corresponds to the native structure or the structure which a mammal produces antibodies against after being infected or immunized with the acid-resistant microorganism or an extract or lysate thereof or a protein therefrom or a fragment thereof or a synthetic peptide; and wherein (b) the formation of at least one antigen-receptor complex according to (a) is detected.

The invention is furthermore based on the objective to provide an immunochromatographic rapid test such as a test strip which is suitable for the detection of one of the above-mentioned infections.

The stool rapid test comprises several layers or areas preferably consisting of optionally different porous materials. The test strip has a sample application area, the test carrier per se (test or analysis area) and an absorber layer (absorption area). In a preferred embodiment, the several layers or regions are fixed on a polyester carrier. In a preferred embodiment, the specific immunological receptors necessary for the detection or, more preferably, the specific antibodies for the antigen are present in dried condition in the sample application area. Preferably, these are labelled with visible coloured particles, e.g. colloidal gold or polystyrene (latex) etc.

More preferably, the test carrier consists of a specific test membrane such as e.g. nitrocellulose. On this test membrane, particularly preferred, further specific receptors which are directed against the antigen are immobilized as test line. As control of the function a further catching line, for example receptors directed against the labelled receptor or antibody may be immobilized. An absorber layer at the end of the test strip advantageously causes the sample flow based on the capillary effect of the porous materials in contact to be maintained.

In the method of the sandwich immunoassay according to the invention, in one of the embodiments, there is a the labelled first specific receptor for the analyte and/or the antigen, for example a labelled antibody (antibody conjugate), is deposited or dried on the sample application area. As test line a second specific receptor for the analyte and/or the analyte is immobilized. During the test, the first specific receptor, e.g. an antibody conjugate is separated and transported via the test membrane. If the specific analyte or the antigen is present in the sample, complexes of the labelled first receptor or antibody conjugate and antigen or analyte are formed during the test. This complex binds to the second specific receptor at the catching line and forms the so-called sandwich complex. Due to the resulting accumulation of the labelled receptors or antibody conjugates at the test line, a visible test signal is created. If there is no analyte or antigen present in the sample, no sandwich complex is formed and no signal is prompted.

In a preferred embodiment of the sandwich method, streptavidin is immobilized at the test line instead of a specific receptor. The specific receptor used as catching receptor for the antigen in the simple sandwich method is conjugated to biotin and placed in the sample application area of the test strip together with a labelled specific receptor. In a particularly preferred embodiment the labelling is colloidal gold. During the test, which consists of a labelled receptor, the antigen and the biotin-labelled receptor, a sandwich complex is formed during their passing the sample application area and the test membrane and is bound at the test line via the biotin-labelled specific receptor by the streptavidin immobilized at that site.

In another preferred embodiment, the gold-labelled specific receptor is located in a first conjugate region of the sample application area of the test strip and the biotin-labelled specific receptor is placed in a second conjugate region of the sample application area.

In another preferred embodiment, the labelled first specific receptor may be replaced by an unlabelled first specific receptor, e.g. antibody. Said first specific receptor is then detected by another labelled receptor that specifically binds said first specific receptor with the other labelled receptor not binding the second specific receptor that is immobilized as test line.

In a further preferred embodiment, the specific second receptor that is immobilized at the test line may be replaced by a second specific receptor that has not been immobilized, e.g. antibody. The analyte-receptor complex is then bound by a receptor that is immobilized at the test line and that binds said non-immobilized second specific receptor with the other immobilized receptor not binding the first labelled specific receptor.

In another particularly preferred embodiment, the non-immobilized second specific receptor is bound to the receptor that is immobilized at the test line.

If antibodies are used, this may be effected, for example, by the fact that the first and the second specific antibody are derived from different species.

The first specific unlabelled receptor may, for instance, be a mouse antibody while the second specific receptor is a rabbit antibody and the other labelled receptor is an anti-mouse antibody.

In a particularly preferred embodiment, the specific unlabelled receptor is located in a first conjugate region of the sample application area of the test strip and the labelled receptor binding the specific unlabelled receptor is located in a second conjugate region of the sample application area of the test strip.

In another particularly preferred embodiment, the first conjugate region is located in flow direction before or above the second conjugate region.

An immunochromatographic rapid test is particularly suitable for putting the present invention into practice. Said test is a dry reagent test with all specific reagents required for the analysis being contained in a test strip consisting of several porous materials, preferably in a dried state. Such a test is based on the principle that the analysis is started by adding a liquid sample and that sample liquid migrates through a test strip consisting of several porous materials due to capillary forces. During migration of the sample liquid, specific binding reagents are dissolved and a complex formation between the analyte contained in the sample and the specific binding reagents takes place. The complexes consisting of the analyte and the specific binding reagents are caught in a defined zone which preferably has the form of a test line by a specific binding reagent immobilized at this testing site. The complexes caught are then made visible due to the aggregation of visible particles coupled with the binding reagents, e.g. dyed polystyrene (latex), colloidal gold, etc. As a consequence, the test of the invention may also be carried out by persons that are not skilled in the art. Furthermore, it offers the possibility of a simple and hygienic use. When the test is carried out, only one step is necessary in the particularly preferred embodiments, i.e. the application of a sample. The result that can be analysed visually is obtained very quickly, i.e. within a few minutes (2–30 minutes).

In another preferred embodiment, the immunochromatographic rapid test of the invention is used in the test device described in WO98/58587. This combination makes it possible that the samples are absorbed, prepared and analysed in a fast and simple manner.

In addition, the rapid test according to the invention avoids the disadvantage existing up to now, i.e. that, when the stool samples are analysed, the sample dissolved in the buffer has a large number of solid substances preventing or complicating the flow of the sample through the fine porous materials of the test strip.

Moreover, the disadvantages in the state of the art, i.e. the fact that stool samples have to be diluted to a great extent, can be avoided. Furthermore, when the method of the invention is carried out, the stool samples diluted in a range of 1:5 and 1:20 do not have to be centrifuged and freed from larger solid substances prior to the test. In addition, the present invention enables a highly sensitive test that can be used independently of a laboratory.

Both a significantly prolonged incubation time for binding the catcher antibody (second receptor) to the antigen (analyte) and a higher affinity of the bond streptavidin/biotin compared to the bond antibody/antigen and therefore an improved binding kinetics at the test line can be achieved particularly by shifting the preferred biotinylated receptor from the test line to the application area although the test strip can—as regards its dimensions—remain almost unchanged.

Within the meaning of the present invention, the term "acid-resistant microorganism" encompasses any microorganism which, due to its properties/mechanisms of adapting to the host, withstands the physical and chemical influence of the digestive tract with the effect that it can be detected by a preferably immunological test or by the use of aptamers. Examples of such acid-resistant microorganisms are *Helicobacter pylori, Helicobacter hepaticum, Mycobacterium tuberculosis, Mycobacterium pseudotuberculosis* and *Mycobacterium cansassii*.

The term "stool sample of the mammal" as used in the present invention means any stool sample that can be used for the detection method of the invention. In particular, it includes stool samples which have been prepared for diagnostic tests according to methods basically known. Preparation may be carried out, for instance, according to RIDASCREEN® Entamoeba enzyme immunoassay (R-Biopharm GmbH, Darmstadt).

The person skilled in the art may readily adjust "conditions permitting complex formation"; cf. also Harlow and Lane, ibid. These conditions are, for example, physiological conditions.

The term "shows [ . . . ] a structure after passage through the intestine that corresponds to the native structure", as used in the present invention, means that the epitope of an antigen is recognised after passage through the intestine by a receptor, e.g. a monoclonal antibody, derivative or fragment thereof or the aptamer which has been obtained against the same antigen/epitope that has not passed the intestine or which is bound thereto. In other words, the epitope/antigen that is specifically bound by the above receptor, has passed the intestine intact or essentially intact as regards its structure and has not been degraded. A source for the native structure of the epitope/antigen may, for instance, be a bacterial extract that was disrupted by means of a French press and further purified according to standard methods (cf., for instance, Sambrook et al., "Molecular Cloning, A Laboratory Manual", $2^{nd}$ edition, 1989, CSH Press, Cold Spring Harbor USA) or a bacterial lysate further purified according to standard methods (e.g. Sambrook et al., ibid.).

The term "shows [ . . . ] a structure after passage through the intestine that corresponds to the structure against which a mammal produces antibodies after being infected or immunised with the acid-resistant microorganism or an extract or lysate thereof or a protein therefrom or a fragment thereof or a synthetic peptide" means according to the invention that the epitope recognised by the receptor corresponds to an epitope which is presented by the immune system of a mammal, preferably a human. The mechanisms of antigen presentation as well as the mechanisms leading to the processing of antigens and the variety of antibodies resulting therefrom have been known in the prior art and have been described, for instance, in Janeway and Travers, Immunologie, $2^{nd}$ edition 1997, Spektrum Akademischer Verlag GmbH, Heidelberg. These epitopes may differ from native epitopes. The contact of the mammal with the microorganisms or proteins or fragments or the synthetic peptides can be brought about by natural infection (except for synthetic peptides) or by immunization. For immunization, also extracts, lysates, synthetic peptides, etc. of the microorganism/protein can be used. Suitable immunization methods have been known in the prior art and have been described, for instance, in Harlow and Lane, ibid. Suitable antibodies may also be obtained, for example, by immunization and/or screening for surrogates such as synthetic peptides, recombinantly produced proteins, extracts, lysates or partially digested proteins.

"Synthetic peptides" comprise peptides having at least one epitope of the native antigen or the antigen which has passed through the intestine. The peptides can have the same primary structure as the antigen or fragments thereof. However, they can also have a different primary structure (primary amino acid sequence, for instance conservative exchanges).

The term "specifically binds", as used herein, means that the receptor shows no or essentially no reactivity with other epitopes in samples of non-infected mammals. Normally, the receptor only binds to an epitope of an antigen that is present in the stool sample.

The term "immune complex", as used herein, comprises complexes comprising monoclonal and/or polyclonal antibodies.

Thus, in this embodiment of the invention a prepared stool sample can, for instance, be bound to a solid phase via a catcher receptor and the infecting agent can be detected with the labelled receptor. If the antigen which is present after having passed the intestine is (still) present in (homo-) dimeric or multimeric form, the same receptor can be used both as a catcher and as a detector.

In addition, it is of importance for the method of the invention that successful detection requires only one epitope of an antigenic protein to be detectable after passage through the intestine in an essentially consistent manner. This epitope can occur several times on a homodimer or -multidimer. The likelihood to find this epitope in detectable form is, however, significantly higher than is the case for a detection test having to rely on more than one epitope to be detected.

Finally, the method of the invention requiring one receptor only involves advantages as regards cost and standardisation.

On the basis of the surprising finding according to the invention that particular antigens from said microorganisms have an epitope structure after passage through the intestine that is essentially consistent to detect, a second embodiment must also be considered essential to the invention. This embodiment is based on the fact that different receptors bind to different epitopes of the same antigen. Here, the term "essentially" means that the epitope(s) and thus a corresponding infection with the microorganism can be detected in more than 70%, preferably at least 75%, more preferably more than 85%, particularly preferred more than 90%, even more preferably more than 95% and most preferably more than 98% of the infected individuals. Ideally, infections are detected in 100% of the infected individuals.

According to the invention, it was surprisingly that by means of only one single receptor which specifically binds an epitope of an antigen of an acid resistant microorganism, or two receptors which specifically bind two epitopes of the same antigen an infection with these bacteria/pathogens can be diagnosed in a relatively reliable way. The invention includes embodiments in which other epitopes having said properties are recognised by other receptors, for instance, by monoclonal antibodies or fragments or derivatives thereof or aptamers. The latter embodiments are suitable for further increasing the reliability of the diagnosis. Advantageously, these other receptors may be antibodies, fragments or derivatives, which specifically recognise urease, preferably β-urease, the 26 kDa protein or Hsp 60, all preferably from H. pylori. The detection of one or more of these proteins/protein fragments may be carried out in the same test or in an independent test with a different part of the same sample.

The results of the invention are surprising mainly because the state of the art taught away therefrom. In the case of H. pylori, for example, it was found that main antigens do not show the desired specificity and sensitivity in ELISA; cf. Newell et al., Serodiag. Immunother. Infect. Dis. 3 (1989), 1–6. Moreover, EP-A-0 806 667 teaches that it is not possible to reliably detect H. pylori infections with receptors, such as monoclonal antibodies due to the genetic variability of H. pylori strains.

Compared to the aforementioned state of the art, the method of the invention is of advantage mainly since it permits a relatively reliable diagnosis with only one receptor. In ELISA or a rapid test, for instance, pairs of receptors, such as antibodies, fragments, derivatives thereof or aptamers are preferably used for detection, with the two receptors of the pair binding the same or different epitopes on the same antigen. *H. pylori* catalase, for example, forms multimeric structures of several identical subunits. Therefore, in ELISA, rapid tests or other assays, the same receptors can be used both as catching receptors and detection receptors.

By combining different monoclonal antibodies directed against different epitopes of the catalase or by combining two detection systems for different antigens (e.g. catalase/urease) an increase in sensitivity and specificity can preferably be achieved. Another advantage of the method of the invention is the fact that it is a direct and non-invasive method, which increases the above-mentioned advantages for patient and the reliability for the stage of the disease to be determined.

Preferred embodiments of the invention are exemplarily described in the following by means of the Figures:

FIG. 1: A cloned DNA sequence coding for the V region of the heavy chain of monoclonal antibody (HP25.2m/2H10) that is specific to catalase (SEQ ID NO:1).

FIG. 2: A cloned DNA sequence coding for the V region of the light chain of a monoclonal antibody (HP25.2m/2H10) that is specific to catalase (SEQ ID NO:2).

FIG. 3: A cloned DNA sequence coding for the V region of the heavy chain of a monoclonal antibody (HP25.6m/1B5) that is specific to catalase (SEQ ID NO:3).

FIG. 4 A cloned DNA sequence coding for the light chain of a monoclonal antibody (HP25.6m/1B5) that is specific to catalase (SEQ ID NO:4).

FIG. 5 A cloned DNA sequence coding for the V region of the light chain of a monoclonal antibody that is specific to β-urease (SEQ ID NO:5).

FIG. 6 A cloned DNA sequence coding for the V region of the heavy chain of a monoclonal antibody that is specific to β-urease (SEQ ID NO:6).

FIG. 7 A cloned DNA sequence coding for the V region of the light chain of a monoclonal antibody that is specific to β-urease (SEQ ID NO:7).

FIG. 8 A cloned DNA sequence coding for the V region of the heavy chain of a monoclonal antibody that is specific to β-urease (SEQ ID NO:8).

FIG. 9 Preparation of a preferred test strip according to the invention.

Figure 10:
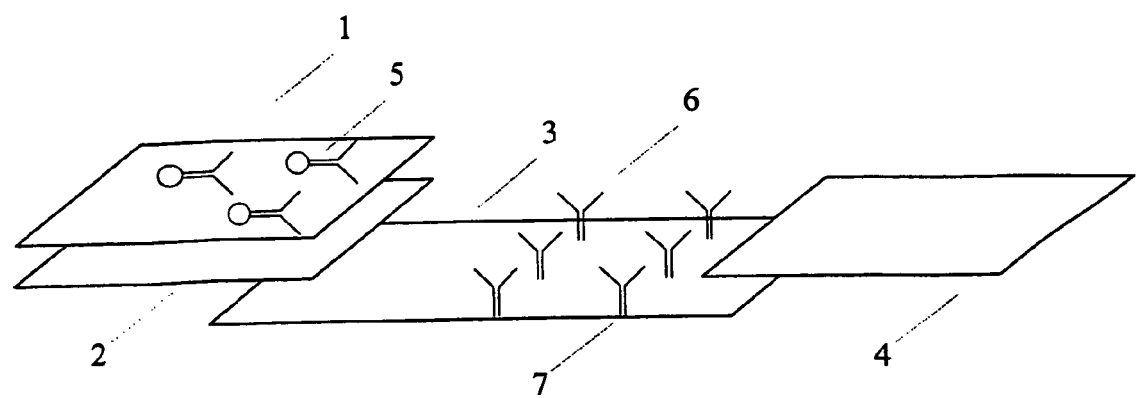

FIG. 10 Preparation of a preferred test strip according to the invention having a control line.

The rapid stool test of the invention according to FIG. 10 consists of a sample application area (1, 2), a test area (test membrane) (3) and an absorption area (4).

In a preferred embodiment, the sample application area (1) consists of two overlying conjugate regions. The upper conjugate region or the conjugate fleece preferably contains the specific receptor labelled, e.g. with gold. The lower conjugate region or the conjugate fleece (not shown) contains, for example, the specific receptor labelled with biotin.

A good flow of the sample and an even distribution of the immune reagents in the sample suspension during the test are of great importance as regards the sensitivity of an immunochromatographic rapid test. Both parameters are influenced mainly by the properties of the porous materials used as well as by their measurements and the their set up in relation to each other.

Furthermore, rapid tests for analyzing stool samples are required to filter the solid substances contained in the sample solution before passing on to the test membrane.

The sample application area of the test consists of a conjugate fleece (1) a subsequent filter (2). The solid substances of the stool suspension, which would prevent the sample from flowing over the test membrane, are separated. The test membranes with which a high sensitivity can be achieved have a distribution of the pore size ranging from 2 to 20 µm, preferably the size if 5 µm. The filter has a separation size of 1–2 µm. Materials made of glass fibre or polyester glass fibre mixtures are particularly suitable. Mixtures of natural and synthetic fibres that were developed for blood separation can also be used.

The following filters, for example, are suitable: Whatman GF/A, GF/B, GF/C, GF/D, F145, F147, F487, GF/DVA; Ahlstrom 111, 141, 142, 151, 164; Pall A/B, A/C, A/D, A/E, A/F. For the conjugate fleece, open-porous material of glass fibre, polyester or polypropylene such as Whatman F 075-14; Schleicher and Schuell GF 10, GF 53, Accuflow P, Accuflow G, Ahlstrom 8980, 2033, 2040, 8975; Millipore QR 01, QR 35, QR 51; QR 61 is suitable.

Apart from its function as conjugate-carrier layer, the conjugate fleece in this set up has the function of a preliminary filter that retains coarse solid substances of the suspended stool sample before they reach the filter. In this set-up it is also of advantage that the sample liquid and the dissolved conjugate flow together through the subsequent filter and that, thus, the incubation time of the analyte or the antigen and the conjugate is prolonged.

The measurements of the conjugate fleece, the filter and the test membrane as well as the transition between the materials of the sample application area are set up in such a way that sufficient filtering of the stool suspension is achieved.

While the sample is applied, the sample liquid is only to be brought in contact with the conjugate fleece but not with the filter.

The set-up of the invention guarantees that a sufficiently large filter area can get in contact with the sample liquid flowing through the conjugate fleece. Furthermore, the set up of the invention enables a minimum distance between the conjugate fleece and the test membrane to make sure that sample liquid that has not been sufficiently filtered does not pass on to the test membrane.

The measurements of the individual regions or materials correspond to the following values:

The preferred breadth of the test strip is between 3 mm and 10 mm, preferably 5 mm. The preferred length of the test strip is 50 to 100 mm, a length of 75 mm is particularly preferred. The preferred length of the conjugate fleece is between 5 to 30 mm, a length of 25 mm is particularly preferred. The overlapping of the conjugate fleece and the filter is preferred to be between 5 and 15 mm, an overlapping of 10 mm is particularly preferred. Filters between 10 and 20 mm are preferred, filters of 15 mm are particularly preferred. The overlapping between the filter and the test membrane is preferred to range from 1 to 3 mm, an overlapping of 1 mm is preferred.

According to the invention, the absorption layer at the end of the test strip (4) has both a sufficient capacity for absorbing the sample liquid that has passed through the test strip and a structure having relatively fine pores for maintaining the capillary effect. Cellulose glass-fibre materials such as Whatman 17 CHR, 3 MM, 31 ET, WF1-5, D28, CD 427-05, CD 427-07, CD 427-08; Schleicher and Schuell 2992, GB 003, GB 004; Pall 111, 11, 133, 165, 197, Ahlstrom 320, 222, 238, 237 proved to be particularly suitable. With test strips having a breadth of 5 mm, a measurement of 10–30 mm for the analysis area is particularly preferred. The overlapping of the test membrane on the absorption layer preferably is at least 1 mm.

The rapid test of the invention is particularly preferred to be used in a device for taking up and analyzing samples as described in WO 98/58587 (PCT/EP98/03764). The subject matter of this document is herewith incorporated into the specification by reference.

In a preferred embodiment, the acid-resistant microorganism is an acid resistant bacterium.

A number of acid-resistant bacteria have been known in the state of the art. In a particularly preferred embodiment the acid-resistant bacterium belongs to the genus *Helicobacter, Campylobacter* or the genus *Mycobacterium*.

In another particularly preferred embodiment, the bacterium is a bacterium belonging to the species *Helicobacter pylori, Helicobacter hepaticum, Campylobacter jeuni* or a bacterium belonging to the species *Mycobactericum tuberculosis*.

In another particularly preferred embodiment, the receptor(s) is/are (an) antibody (antibodies), (a) fragment(s) or (a) derivative(s) thereof or (an) aptamer(s).

The term "receptor' as used herein, however, comprises further binding partners such as avidin, streptavidin or polystreptavidin and biotin.

Within the meaning of the present invention, "fragments" or "derivatives" of monoclonal antibodies have the same binding specificity as the monoclonal antibodies. Such fragments or derivatives can be produced according to standard methods; cf. for example Harlow and Lane, "Antibodies, A Laboratory Manual", CSH Press, Cold Spring Harbor, USA, 1988. Examples of fragments include Fab-, F(ab')$_2$ or Fv-fragments. scFv fragments are examples of derivatives. Derivatives can also be chemically produced substances having the same or binding properties as the antibodies or improved binding properties. Such substances can be generated, for instance, by peptidomimetics or by different cycles of phage display and subsequent selection as to improved binding properties. According to the invention, aptamers are nucleic acids such as RNA; ssDNA (ss=single-stranded), modified RNA or modified ssDNA, which bind a large number of target sequences having specificity and affinity. The term "aptamer" has been known and defined in the prior art, for example, in Osborne et al., Curr. Opin. Chem. Biol. 1 (1997), 5–9 or in Stull and Szoka, Pharm. Res. 12 (1995), 465–483.

The term "antigen-antibody complex" within the meaning of the present invention does not only comprise complexes the antigen forms with the native antibody, but also those which it forms with the fragments or derivatives thereof.

The invention comprises embodiments in which only monoclonal antibodies or fragments or derivatives thereof or only aptamers are used as well as embodiments in which different types of detection reagents are used in one test. Hence, it is possible for a first monoclonal antibody to be used with a second antibody derivative or a first aptamer to be used with a second antibody fragment, to name only two examples. In this respect, the terms "first" and "second" refer to the first and the second detection reagent. This, however, does not mean that two antibodies, derivatives or fragments thereof or two aptamers are always used.

The use of monoclonal antibodies, fragments or derivatives thereof or of aptamers ensures easy maintenance of a standard in the reliability of the diagnosis method, which means a great advantage compared to diagnosis methods that have been known so far and that have been introduced for this purpose. Moreover, it is no longer necessary to keep immunizing and subsequently testing new test animals as is required, for instance, in the method according to EP-A 0 806 667.

In another preferred embodiment the antigen is the antigen of a catalase, preferably from *H. pylori*. The catalase has the special advantage that it could be detected in all acid resistant bacteria known so far. According to the invention it was found, as another advantage, that the catalase is very resistant to digestion in the intestinal tract, which simplifies detection of significant amounts. After all, the catalase or fragments thereof is/are still present in a superior structure, for instance in tetrameric form, after having passed the intestine, which facilitates detection with one receptor type only.

According to the invention, it has surprisingly been found that in a population of mammals, in particular human patients, whose stools had been tested for infections with acid-resistant bacteria, essentially all members of this population showed consistently recurring catalase epitopes in the stool, with the result that it is very likely to make a relatively reliable diagnosis with only one corresponding receptor, preferably monoclonal antibodies, fragments or derivatives thereof or aptamers. In particular, since the catalase possesses a tetrameric antigenic structure, this diagnosis can advantageously be made, for instance, in ELISA, immunochromatographic rapid test or in similarly arranged solid systems.

The catalase is particularly preferred to be the catalase of *H. pylori*.

In another preferred embodiment the antigen is a metalloproteinase, the metalloproteinase of *H. pylori* is particularly preferred.

In another preferred embodiment the antigen is a urease, preferably from *H. pylori*.

In another preferred embodiment, additional use is made of a mixture of receptors for the detection, with the mixture of receptors having the function of a catcher of the antigen if the receptor is used as detector of the antigen, and the mixture having the function of a detector of the antigen if the receptor is used as catcher of the antigen. For the detection both different and the same mixture(s) of receptors can be used as catcher and detector of the antigen: If the same mixture is used both as catcher and detector of the antigen, the catcher preferably is labelled and the detector is immobilized on the test line.

This embodiment of the invention permits a particularly reliable diagnosis, especially, if the antigen is not present in a dimeric or multimeric conformation after passage through the intestine. This embodiment makes it possible for only one of the two receptor types used in the majority of the standardized immunological detection methods to be a monoclonal antibody, while, for instance, the second receptor type may be a polyclonal serum.

In a particularly preferred embodiment, the mixture of receptors is a polyclonal antiserum.

In another particularly preferred embodiment, mixtures of receptors are used for detection with one mixture of receptors serving as catcher of the antigen and one mixture of receptors serving as detector of the antigen and preferably at least one mixture being a polyclonal serum.

In another particularly preferred embodiment, a mixture of receptors serves both as catcher and as detector of the antigen with the mixture preferably being a polyclonal antiserum.

In an additionally particularly preferred embodiment, the polyclonal antiserum was obtained against a lysate of the microorganism, preferably *H. pylori*.

In another particularly preferred embodiment, the lysate is a lysate with an enriched antigen.

In another preferred embodiment, the lysate is a lysate with depleted immunodominant antigen.

The two aforementioned embodiments also include the fact that the lysate is a lysate with enriched antigen, preferably with enriched catalase and with depleted immunodominant antigen, preferably mainly antigenic urease. In particular, said combination offers the possibility of obtaining a high immunization yield, which is especially suitable for the method of the invention. A way of carrying out corresponding enrichment and depletion methods is described in more detail in the examples.

According to another particularly preferred embodiment, the polyclonal antiserum against a purified or (semi) synthetically produced antigen was obtained, which preferably is a catalase, metalloprotease or urease enzyme, preferably from H. pylori.

According to the invention, the receptors, preferably the monoclonal antibodies, fragments or derivatives thereof or the aptamers can recognise and specifically bind linear or conformation epitopes. In another preferred embodiment, at least one of the receptors binds a conformation epitope.

In a particularly preferred embodiment, all receptors bind conformation epitopes.

In a particularly preferred embodiment, the heavy chain of the antibody [HP25.2m/2H10] binding a catalase epitope has at least one of the following CDRs, preferably the CDR3 and still more preferably all of the following three CDRs:

```
CDR1:    NYWIH (SEQ. ID NO.: 9)
CDR2:    YINPATGSTSYNQDFQD (SEQ. ID NO.: 10)
CDR3:    EGYDGFDS (SEQ. ID NO.: 11)
```

In another particularly preferred embodiment, the DNA sequence encoding the heavy chain of the antibody [HP25.2m/2H10]binding a catalase epitope has at least one of the following CDRs, preferably the CDR3 and still more preferably all of the following CDRs:

```
CDR1: AACTACTGGA TTCAC (SEQ. ID NO.: 12)

CDR2: TACATTAATC CTGCCACTGG TTCCACTTCT TACAATCAGG
      ACTTTCAGGA C (SEQ. ID NO.: 13)

CDR3: GAGGGGTACG ACGGGTTTGA CTCC (SEQ. ID NO.: 14)
```

In another particularly preferred embodiment, the light chain of the antibody [HP25.2m/2H10] binding a catalase epitope has at least one of the following CDRs, preferably the CDR3 and still more preferably all of the following CDRs:

```
CDR1:    SASSSVNYMY (SEQ. ID NO.: 15)
CDR2:    DTSKLAS (SEQ. ID NO.: 16)
CDR3:    QQWSSNPYT (SEQ. ID NO.: 17)
```

Furthermore, in another particularly preferred embodiment, the DNA sequence encoding the light chain of the antibody [HP25.2m/2H10] has at least one of the following CDRs, preferably the CDR3 and still more preferably all of the following CDRs:

```
CDR1:
AGTGCCAGCT CAAGTGTAAA TTACATGTAC (SEQ. ID NO.: 18)

CDR2:
GACACATCCA AATTGGCTTC T (SEQ. ID NO.: 19)

CDR3:
CAGCAGTGGA GTAGTAATCC GTACACG (SEQ. ID NO.: 20)
```

In a particularly preferred embodiment, the heavy chain of the antibody [HP25.6m/1B5] binding a catalase epitope has at least one of the following CDRs, preferably the CDR3 and still more preferably all of the following CDRs:

```
CDR1:    DTYVH (SEQ. ID NO.: 21)
CDR2:    KIDPANGKTKYDPIFQA (SEQ. ID NO.: 22)
CDR3:    PIYYASSWFAY (SEQ. ID NO.: 23)
```

In another particularly preferred embodiment, the DNA sequence encoding the heavy chain of the antibody [HP25.6m/1B5] binding a catalase epitope has at least one of the following CDRs, preferably the CDR3 and still more preferably all of the following CDRs:

```
CDR1:
GACACCTATGTGCAC (SEQ. ID NO.: 24)

CDR2:
AAGATTGATCCTGCGAATGGTAAAACTAAATATGACCCGATAT
CCAG GCC (SEQ. ID NO.: 25)

CDR3:
CCCATTTATTACGCTAGTTCCTGGTTTGCTTAC
(SEQ. ID NO.: 26)
```

In another particularly preferred embodiment, the light chain of the antibody [HP25.6m/1B5] binding a catalase epitope has at least one of the following CDRs, preferably the CDR3 and still more preferably all of the following CDRs:

```
CDR1:    KASQDVGTSVA (SEQ. ID NO.: 27)
CDR2:    WTSTRHT (SEQ. ID NO.: 28)
CDR3:    QQYSSSPT (SEQ. ID NO.: 29)
```

Moreover, in a particularly preferred embodiment, the DNA sequence encoding the light chain of the antibody [HP25.6m/1B5] binding a catalase epitope has at least one of the following CDRs, preferably the CDR3 and still more preferably all of the following CDRs:

```
CDR1:
AAGGCCAGTCAGGATGTGGGTACTTCTGTTGCC (SEQ. ID
NO.: 30)

CDR2:
TGGACATCCACCCGGCACACT (SEQ. ID NO.: 31)

CDR3:
CAGCAATATAGCAGCTCTCCCACG (SEQ. ID NO.: 32)
```

In another preferred embodiment, the antibody specific to β-urease is the antibody which has been generated by the hybridomas HP8m/4H5-D4-C9 or HP9.1m/3C2-F8-E2 deposited with the German Collection of Microorganisms and Cell Cultures (Deutsche Sammlung von Mikroorganismen und Zellkulturen DSMZ) on Jun. 23, 1998 in accordance with the Statutes of the Budapest Treaty under the accession numbers DSM ACC2360 or DSM ACC2362. The antibody specific to β-urease [HP8m/1H5-G2-B4] which is described in the Figures is produced by a daughter clone of the deposited hybridoma HP8 m/4H5-D4-C9. Both antibodies produced by the mother and the daughter clone are encoded by identical DNA sequences and have the same properties.

In another particularly preferred embodiment of the method of the invention, the heavy chain of the antibody binding an epitope of the β-urease has at least one of the following CDRs, preferably the CDR3 and still more preferably all of the following CDRs:

```
CDR1:    GFTFSSHFMS (SEQ. ID NO.: 33)

CDR2:    SISSGGDSFYPDSLKG (SEQ. ID NO.: 34)

CDR3:    DYSWYALDY (SEQ. ID NO.: 35)

or:

CDR1:    GYAFSTSWMN (SEQ. ID NO.: 36)

CDR2:    RIYPGDGDTNYNGKFKG (SEQ. ID NO.: 37)

CDR3:    EDAYYSNPYSLDY (SEQ. ID NO.: 38)
```

In another particularly preferred embodiment, the DNA sequence encoding the heavy chain of the antibody binding an epitope of the β-urease has at least one of the following CDRs, preferably the CDR3 and still more preferably all of the following CDRs:

```
CDR1:
GG CTACGCATTC AGTACCTCCT GGATGAAC (SEQ. ID NO.:
39)

CDR2:
CGGATTTATC CTGGAGATGG AGATACTAAC TACAATGGGA
AGTTCAAGGG C (SEQ. ID NO.: 40)

CDR3:
GAG GATGCCTATT ATAGTAACCC CTATAGTTTG GACTAC
(SEQ. ID NO.: 41)

or:

CDR1:
GG ATTCACTTTC AGTAGCCATT TCATGTCT (SEQ. ID NO.: 42)

CDR2:
TCCATTAGTA GTGGTGGTGA CAGTTTCTAT CCAGACAGTC
TGAAGGGC (SEQ. ID NO.: 43)

CDR3:
GACTAC TCTTGGTATG CTTTGGACTA C (SEQ. ID NO.: 44)
```

In another particularly preferred embodiment of the method of the invention, the light chain of the antibody binding an epitope of the β-urease has at least one of the following CDRs, preferably the CDR3 and still more preferably all of the following CDRs:

```
CDR1:    RASQSIGTRIH (SEQ. ID NO.: 45)

CDR2:    YGSESIS (SEQ. ID NO.: 46)

CDR3:    QQSNTWPLT (SEQ. ID NO.: 47)
```

```
or:

CDR1:    HASQNINVWLS (SEQ. ID NO.: 48)

CDR2:    KASNLHT (SEQ. ID NO.: 49)

CDR3:    QQGRSYPLT (SEQ. ID NO.: 50)
```

In addition, the DNA sequence encoding the light chain of the said antibody preferably has the following CDRs:

```
CDR1:
A GGGCCAGTCA GAGCATTGGC ACAAGAATAC AC
(SEQ. ID NO.: 51)

CDR2:
TAT GGTTCTGAGT CTATCTCT (SEQ. ID NO.: 52)

CDR3:
CAACAA AGTAATACCT GGCCGCTCAC G (SEQ. ID NO.: 53)

or:

CDR1:
C ATGCCAGTCA GAACATTAAT GTTTGGTTAA GC (SEQ. ID
NO.: 54)

CDR2:
AAG GCTTCCAACT TGCACACA (SEQ. ID NO.: 55)

CDR3:
CAACAG GGTCGAAGTT ATCCTCTCAC G (SEQ. ID NO.: 56)
```

In addition, it is preferred that the heavy and light chains having said CDRs occur together with one antibody, fragment or derivative thereof, which specifically binds the catalase or the β-urease or a fragment thereof, preferably from H. pylori. Yet, the invention also comprises embodiments in which these heavy or light chains are combined with other light or heavy chains, wherein these binding properties may essentially be maintained or improved. Corresponding methods have been known in the prior art. Particularly preferred antibodies have in the variable regions of the light and heavy chains the amino acid sequences shown in FIGS. 1 and 2, 3 and 4, 5 and 6 or 7 and 8 or the regions are encoded by the DNA sequences shown therein. According to methods known in the state of the art, the CDRs may be integrated in various FRs (framework regions).

In a particularly preferred embodiment, the following steps are carried out with the stool sample before incubation with the antibodies: the stool sample is resuspended in a sample buffer at a ratio of 1:3 to 1:25, preferably of 1:15. Such sample buffers are known in the state of the art. An example of a sample buffer is: 150 mM PBS, 0.1% SDS.

In a preferred embodiment, the sample buffer consists of 150 mM PBS, 0.5% serum and 2% detergent. The serum can be obtained from cow, mouse, rat, pig or human and the detergent can be selected from a group of ionic (preferably Tween 20) and non-ionic detergents (preferably SDS).

In another embodiment, the detection according to the invention may also be used for the detection of H. pylori in gastric gas, breath condensate, saliva, tooth plaque, mucous smear, biopsies, whole blood or serum. Breath gases can be obtained by giving the patient cold $CO_2$-containing drinks causing the release of gastric gas in the form of "burping". Said gas can be collected in suitable containers or breath condensate can be recovered in a manner known to the skilled person, e.g. by means of a device according to DE 19718925 or a device according to DE 19505504. The condensates obtained in such a way can then be introduced in a liquid form into the test of the invention with all the steps of the method of the invention as has been described earlier being carried out, except that a sample as described herein is used instead of a stool sample. Tooth plaque and mucous smear can be obtained according to methods known in the state of the art and can, like saliva, whole blood and serum, be used for the detection according to the invention in appropriate concentrations as well as with modifications of the resuspension buffer.

In another preferred embodiment, the formation of at least one antigen-receptor complex/antigen-receptor-receptor mixture complex in step (b) is detected by means of an immunolochromatographic method.

In a particularly preferred embodiment of the method of the invention, in the immunologic method the same receptor is used for both binding to the solid phase and detecting the epitope. While the catcher receptor can be bound to a solid phase, e.g. nitrocellulose, in an unmodified form, the receptor used for detection may optionally be labelled.

In another preferred embodiment, the catcher receptor may be present in a biotinylated form and be bound to the solid phase by means of streptavidin immobilized on the solid phase.

On the other hand, the catcher receptor may not be labelled with biotin and the epitope of the microorganism, preferably the bacterial epitope, may be detected via a third biotin-labelled receptor, this receptor preferably being an antibody, fragment or derivative thereof or an aptamer, or a species-specific or lg class-specific antibody or a corresponding aptamer. Said third biotin-labelled receptor specifically binds the catcher receptor, and the analyte-receptor complex is bound, via the third biotin-labelled receptor, to the test line, which in this embodiment consists of immobilized streptavidin.

Colloidal gold, selenium, coloured polystyrene or latex particles, carbon particles as well as disperse colours (which the skilled person knows from the state of the art) can be used as labellings for the receptor used for detection.

On the other hand, as has been mentioned before, the receptor used for detection may also not be labelled and thus, the epitope of the microorganism may be detected via a third labelled receptor directed against said unlabelled receptor, said receptor preferably being an antibody, fragment or derivative thereof or an aptamer, which may be a species-specific or lg class-specific antibody or a corresponding aptamer.

In a particularly preferred embodiment, the labelling is colloidal gold.

Such labellings are known in the state of the art; cf. Harlow and Lane, loc. cit. The same applies to apatamers. The embodiment described before is of particular advantage as regards the detection of catalase which optionally is still present as tetramer after passage through the intestine. Of course, also in this embodiment combinations of antibodies, fragments, derivatives and aptamers may be used, e.g. combinations of antibodies, etc., which bind to different epitopes of the same antigen.

In another preferred embodiment of the method of the invention, the monoclonal antibody is a murine antibody.

In addition, in another preferred embodiment, the receptors are fixed to a support.

When carrying out routine checks, it is of particular advantage to fix the receptors, preferably the antibody, fragments or derivatives thereof or the aptamers to a support.

Moreover, the combination antibody-support/aptamer-support may be packaged as a tool set or in the form of a kit.

In another particularly preferred embodiment, the material of the support is a porous support material.

In another particularly preferred embodiment, the support material is a test strip.

In addition, in a preferred embodiment, the support material consists of cellulose or a cellulose derivative.

The mammal whose stool, gastric gas, breath condensate, saliva, tooth plaque, mucous smear, biopsy, whole blood or serum can be analysed by means of the method of the invention may be an animal, e.g. a domestic animal such as a cat or a dog, a useful animal such as a pig or another kind of animal such as a mouse, a tiger, a gerbil or a ferret.

In another preferred embodiment, the mammal is a human.

In another preferred embodiment, the method of the invention is an automated method. An automated method may, for instance, be carried out by means of a robot, with the robot carrying out some or all steps of the procedure. Corresponding robots are known in the state of the art.

Furthermore, the invention relates to a monoclonal antibody, a fragment or derivative thereof having a V region which has a combination of the aforementioned CDRs or which is produced by one of the aforementioned hybridomas.

In this case, monoclonal antibodies, fragments or derivatives thereof are preferred which have at least one of the V regions depicted in FIGS. 1 and 2, 3 and 4, 5 and 6 or 7 and 8. Preferably, this antibody has two of the V regions shown in FIGS. 1 and 2, 3 and 4, 5 and 6 or 7 and. Moreover, these V regions are preferred to be encoded by the DNA sequences shown in FIGS. 1 and 2.

In a particularly preferred embodiment of the invention, the monoclonal antibody, the fragment or derivative thereof is a murine antibody or a fragment or derivative thereof or a chimeric, preferably a humanized antibody or a fragment or derivative thereof. The derivative may also be a fusion protein. Furthermore, the antibody is preferred to be labelled, for instance with a colloid, a labelling consisting of gold, selenium, latex, coloured polystyrene, carbon particles in disperse colours known to the person skilled in the art. with a radioactive, fluorescent, phosphorescent or chemiluminescent labelling.

The production of chimeric humanized and human antibodies and of the other derivatives has been well known in the state of the art (e.g. Vaughan et al., 1998; Orlandi et al., 1989, Harlow and Lane, ibid.).

The invention also related to an aptamer which specifically binds the same epitope as the monoclonal antibody, the fragment or derivative thereof. Such aptamers can be produced according to methods known in the state of the art.

In addition, the invention relates to an epitope which is specifically bound by one of the above-described antibodies, fragments or derivatives thereof or aptamers.

Furthermore, the invention relates to further antibodies, derivatives or fragments thereof, which specifically bind the epitope of the invention. These antibodies may, for instance, be monoclonal antibodies which can be produced according to standard methods using the epitope as a hapten/component of an antigen.

Moreover, the present invention relates to a diagnostic composition containing at least one receptor, preferably at least one monoclonal antibody, fragment or derivative thereof or aptamers as defined above, fixed to a support material.

Furthermore, the present invention relates to a test device for detecting at least one of the above-defined epitopes, comprising (a) at least one receptor which is preferred to be a monoclonal antibody, fragments or derivatives thereof or an aptamer as defined above, fixed to a support material; (b) a device for preparing and analysing stool samples and optionally, a mixture of receptors as defined above.

As has been mentioned before, the invention additionally relates to a device for preparing and analysing stool samples as described in WO 98/58587. Said device contains units for the absorption and preparation of the sample and a test unit (test strip) in one apparatus.

A further subject-matter of the invention is a test device comprising (a) at least one receptor, preferably a monoclonal antibody, fragments or derivatives thereof or an aptamer as defined above, with the receptor being conjugated with colloidal gold, polystyrene (latex) or other colouring particles the size of which typically ranges from 5 nm to 100 nm, preferably from 40 nm to 60 nm (a particle size of 40 nm to 60 nm for gold and of 200 nm to 500 nm for latex is particularly preferred); (b) a device for preparing and analysing stool samples as described in WO 98/58587; and optionally (c) a mixture of receptors as defined above.

Alternatively to the devices for preparing and analysing stool samples, the compositions and kits may also have devices for preparing (if necessary) and analyzing gastric gases, breath condensate, saliva, tooth plaque, mucous smear, biopsies, whole blood or serum.

Furthermore, the present invention relates to a kit containing (a) at least one receptor which preferably is a monoclonal antibody, fragments or derivatives thereof or an aptamer as defined above and which is fixed to a support material; optionally also (b) a device for preparing and analysing stool samples as described, for instance, in WO 98/58587; and optionally (c) a mixture of receptors as defined above.

The Figures illustrate:

FIG. 1: A cloned DNA sequence (SEQ ID NO:1) coding for the V region of the heavy chain of monoclonal antibody [HP25.2m/2H10] specific to catalase. The encoded amino acid sequence (SEQ ID NO:83) is shown in a single-letter code. The CDR regions 1–3 determined according to Kabat et al. are underlined.

FIG. 2: A cloned DNA sequence (SEQ ID NO:2) coding for the V region of the light chain of a monoclonal antibody [HP25.2m/2H10] specific to catalase. The encoded amino acid sequence (SEQ ID NO:84) is shown in single-letter code. The CDR regions 1–3 determined according to Kabat et al. are underlined.

FIG. 3: A cloned DNA sequence (SEQ ID NO:3) coding for the V region of the heavy chain of a monoclonal antibody [HP25.6m/1B5] specific to catalase. The encoded amino acid sequence (SEQ ID NO:85) is shown in a single-letter code. The CDR regions 1–3 determined according to Kabat et al. are underlined.

FIG. 4: A cloned DNA sequence (SEQ ID NO:4) coding for the V region of the light chain of a monoclonal antibody [HP25.6m/1B5] specific to catalase. The encoded amino acid sequence (SEQ ID NO:86) is shown in a single-letter code. The CDR regions 1–3 determined according to Kabat et al. are underlined.

FIG. 5: DNA sequence (SEQ ID NO:5) coding for a light chain of a first monoclonal antibody (DSM ACC2360) specific to urease. The encoded amino acid sequence (SEQ ID NO:87) is shown in single-letter code. The CDR regions 1–3 determined according to Kabat et al. are underlined.

FIG. 6: DNA sequence (SEQ ID NO:6) coding for a heavy chain of a first monoclonal antibody (DSM ACC2360) specific to urease. The encoded amino acid sequence (SEQ ID NO:88) is shown in single-letter code. The CDR regions 1–3 determined according to Kabat et al. are underlined.

FIG. 7: DNA sequence (SEQ ID NO:7) coding for a light chain of a second monoclonal antibody (DSM ACC2362) specific to urease. The encoded amino acid sequence (SEQ ID NO:89) is shown in single-letter code. The CDR regions 1–3 determined according to Kabat et al. are underlined.

FIG. 8: DNA sequence (SEQ ID NO:8) coding for a heavy chain of a second monoclonal antibody [DSM ACC2362] specific to urease. The encoded amino acid sequence (SEQ ID NO:90) is shown in single-letter code. The CDR regions 1–3 determined according to Kabat et al. are underlined.

FIG. 9: General set-up of a rapid-test strip: sample application area (1); test or analysis area (3), absorption area (4). In the sample application area, there are the receptors (in a dried state) necessary for the detection, e.g. specific antibodies for the analyte or the antigen which are labelled with, e.g. colloidal gold or polystyrene (latex) or other binding partners. Most of the time, the test carrier consists of a special test membrane such as nitrocellulose. On said test membrane, additional specific receptors directed against the analyte or the antigen are immobilized as a test line. There is a filter (2) between the sample application area and the test area.

FIG. 10: Set-up of a rapid-test strip with control line: sample application area (1); test or analysis area (3) and absorption area (4). In the sample application area, there are the receptors (in a dried state) necessary for the antigen, which are labelled with visible coloured particles, e.g. colloidal gold or polystyrene. In a preferred embodiment, the sample application area may consist of two overlapping conjugate regions which contain in one region, for instance, the gold-labelled receptor, in the other region a biotin-labelled receptor. The test carrier mostly consists of a special test membrane, e.g. nitrocellulose. On this test membrane, additional specific receptors directed against the analyte (antigen) are immobilized as test line (6). In a preferred embodiment, streptavidin may be immobilized as a test line. As a function control another control or catching line (7), e.g. a receptor directed against the labelled receptor, can be immobilized on the test membrane. Between the sample application area and the test carrier, there is a filter (2).

The Examples illustrate the invention.

EXAMPLE 1

Isolation of *H. Pylori* Antigens

Cultivation of *H. Pylori*

*H. pylori* (strain NCTC 11637) was plated in petri dishes on Wilkins chalkers agar adding 10% horse blood and Amphotericin B, Vancomycin and Cefsoludin (Sigma Chemicals) and incubated in an microaerophile atmosphere (Anaerocult GasPAk, Merck) at 37° C. for 3 or 4 days. The content of 2 dishes was suspended in a 1 1-bottle (Schott) in 350 ml of BHIB medium adding the antibiotics as above, the medium was fumigated for 10 min with a gas mixture of 10% $CO_2$, 5% $O_2$, 85% $N_2$ and the bottle was sealed. The culture was shaken on a rotary shaker for 2 days at 37° C. Then, the content of the bottle was put aseptically in a 10 l-bottle and filled up with 4, 7 l BHIB-medium. It was incubated on a rotary shaker for another 2 days at 37° C. Subsequently, the whole volume was centrifuged at 5,000 g for 15 min, the supernatant was decanted and the bacteria pellet was weighed. In order to store the pellet, it was resuspended in a physiological saline solution adding 15% glycerine at a ratio of 2:1 (w/v) and frozen at −80° C. In order to check the identity of the cultivated bacteria, a microscopic inspection of the bacteria as well as tests for urease, oxidase and catalase activity were carried out.

EXAMPLE 2

Preparation of H. Pylori Antigens

Preparation of H. Pylori Lysate

PBS, pH 7.5 was added to H. pylori bacteria pellet (Example 1) at a ratio of 1:10 and resuspended on ice. The bacteria cells were sonicated on ice with a small ultrasonic detector (Sonifer, Branson) with an intensity of 25–30% for 10×60 s with a break of 60 s each. The disrupted bacteria cells were centrifuged 2×20 min at 4° C. and 10,000 rpm (Sorvall, SS34). The supernatant was used as antigen preparation for the production of polyclonal antisera.

Preparation of H. Pylori Catalase

Disruption buffer (20 mM Tris HCl, pH 7.0, 1 mM EDTA, 1 mM phenyl methyl sulfonyl fluoride (PMSF), 0.05% sodium azide and 10% (v/v) isobutanol) was added to frozen bacteria pellet at a ratio of 1:2 (w/v) and shaken at room temperature (RT) in an overhead shaker until complete thawing and subsequently shaken for another approximately 15 min. After centrifugation at 20,000 rpm (Sorvall, SS-34), 4° C. for 20 min, the supernatant was decanted and filtered through a 0.45 μm-filter.

The clear supernatant was diluted with buffer A (20 mM Tris HCl pH 7.0, 1 mM EDTA, 1 mM PMSF, 0.05% sodium azide) at a ratio of 1:3 and transferred onto a SourceQ column (16/10) (Pharmacia) equilibrated with buffer A. The flow through of the SourceQ column contained the enzyme catalase and was free of H. pylori main antigens such as urease, Hsp60 and alkylhydroperoxide reductase.

In order to isolate the katalase, the flow through of the SourceQ column was subjected to a molecular sieve chromatography (Superdex 200) (16/60). The catalase was isolated together with another protein with a size of approx. 150 kDa (neutrophil activating protein, NAP) in about equal shares.

Catalase with a higher purity was obtained when the flow through of the SourceQ-column was put in a 2 M sodium acetate solution, pH 4.9, on 40 mM sodium acetate and was transferred on a SourceS column (8/28). After washing with buffer A to remove the proteins that are not bound, the catalase was eluted with buffer B (40 mM sodium acetate, 1 M NaCl, pH 4.9) using a linear NaCl gradient (buffer A plus 0% to 100% of buffer B). Catalase elutes at approx. 370 mM NaCl.

EXAMPLE 3

Characterization of the Catalase

Under reducing conditions in SDS PAGE, the purified protein had a molecular weight of approx. 58 kDa and a purity of ≧90%.

In order to identify the isolated protein, a micro sequencing was carried out. The protein was cleaved in SDS PAGE gel with LysC protease. The extracted protein mixture was separated via RP-HPLC. The sequence analysis of the LysC peptide resulted in the following amino acid sequence:

ERLHDTIGESLAHVTHK (SEQ ID NO: 57)

This sequence is identical to the corresponding LysC peptide from H. pylori catalase (Manos J. et al. (1998) Helicobacter 3 (1), 28–38; Genbank accession no. AAC16068.1).

EXAMPLE 4

Production of Polyclonal and Monoclonal Antibodies (pAk; mAk)

Production of Polyclonal Antisera:

Polyclonal antisera against H. pylori lysate, H. pylori lysate with depleted main antigens such as urease, Hsp60 and alkylhydroperoxide reductase (cf. Example 2: isolation and purification), H. pylori lysate with enriched catalase (for example by adding catalase to the lysate), as well as polyclonal antisera against purified catalase can be obtained by immunizing a selected mammal (e.g. mouse, rabbit, goat, etc.) with the corresponding immunogenic preparations containing the catalase epitope.

The antibodies can be purified by means of protein A affinity chromatography of sera and can be used as catching antibodies in sandwich ELISA (cf. Example 9) for assessing whether the monoclonal antibodies are suitable for antigen detection in the stool of patients.

Polyclonal rabbit antisera were generated by pab Productions (Herbertshausen) from H. pylori lysate. By means of protein A affinity chromatography polyclonal antibodies were purified from these antisera and used as catching antibodies in Sandwich ELISA (cf. Example 9) for assessing whether the monoclonal antibodies are suitable for antigen detection in the stool of patients.

Production of Monoclonal Antibodies:

The monoclonal antibodies were generated according to methods known to the person skilled in the art (Harlow & Lane, 1988; Peters & Baumgarten, 1990).

Immunization

Antigen preparations produced from H. pylori lysate (cf. Example 2) were used for immunizing mice (BALB/c×C57/Black, F1 generation, 8–12 weeks old). For basic immunization 50 μg antigen were emulsified with Freund complete adjuvant (Difco) and injected intraperitoneally (200 μl/mouse). In booster shots every four months, the mice were given 25 μg antigen each with Freund incomplete adjuvant. An antiserum as positive control in ELISA (cf. fusion screening) was obtained from blood taken retro-orbitally from the mice.

Fusion

Two days after the last immunization, the spleens of the mice were removed and the spleen cells were fused with the myeloma cells P3×63Ag8.653 (ATCC CRL-1580; Kearney et al., 1979) with polyethylene glycol 4000 at a ratio of 5:1. The fused cells were suspended in HAT medium (cloning medium (=RMI 1640 medium, 20% FCS, 200 U/ml rhIL-6) with hypoxanthine aminopterin thymidine supplement (Sigma)) and plated in 96-dish micro titre plates with a cell density of 2-6$10^4$ cells/dish. The hybridomas were cultivated at 37° C., 5% $CO_2$ and 95% relative humidity.

Fusion Screening by Means of Direct ELISA

Screening of the antibody-containing culture supernatants from colonized dishes (approx. 10 days after the fusion) was carried out in direct ELISA on 96-dish micro titre plates (maxiSorb, Nunc):

The ELISA plates were coated with 2 μg/ml immunization antigen in carbonate buffer, pH 9.6 (100 μl/dish, over night 5° C.). The coating solution was sucked off and binding sites that were still free were blocked with 2% skimmed-milk powder in PBS (w/v) (200 µl/dish, 1 hour, room temperature). After washing the plate twice with PBS, pH 7.3 with 0.025% Tween 20 (v/v), the culture supernatants of the primary clones were pipetted undiluted in the dishes (100 µl/dish) and the plates were incubated for 1–2 hours at room temperature. The antiserum was used as a positive control, the medium as a negative control. After washing again, the detection of the bound antibodies was carried out with a peroxidase-labelled secondary antibody (rabbit-anti-mouse Ig-POD (DAKO) in PBS with 0.1% bovine serum albumin, 20 min., room temperature). After washing and knocking the plate four times, the substrate solution (K-Blue, Neogen or citric acid buffer, pH 4.5, with TMB+$H_2O_2$) was added. The peroxidase turns the colourless substrate tetramethyl benzidine (TMB, Sigma) into a coloured complex. After 10 min the reaction was stopped by adding 1 N sulfuric acid. Culture supernatants of clones producing antigen-specific antibodies were significantly coloured compared to the colourless negative culture supernatants.

Establishing and Cultivating the Hybridomas

Positive clones were recloned twice according to the principle of limiting dilution analysis in order to obtain monoclones (Coller & Coller, 1983). The first recloning was carried out in cloning medium with hypoxanthine thymidine supplement (Sigma), the second one in cloning medium. The reclones were examined for antigen specificity by means of direct ELISA. In the end, the final clone was adapted to production medium (RPMI 1640 Medium with 5% IgG-reduced FCS) in flat bottles. The cells were cryo-preserved and the culture supenatant was produced for the antibody purification.

EXAMPLE 5

Characterization of the Antibodies from the Culture Supernatant 10 clones were selected from a repertoire of 30 specific (producing antibodies against the immunization antigen) clones by means of their good reactivity to stool samples of patients infected with *H. pylori* in Sandwich EL1SA (cf. Table 2).

Isotyping

In the culture supernatant isotyping of the monoclonal antibody was carried out with the establishing clones using the isotyping Kit IsoStrip (Roche Diagnostics). The result was: 8 type IgG1-clones and one type IgG2a-clone (cf. Table 2).

Western Blot

In Western blot, the culture supernatants were examined for their ability to specifically recognize the Immunizing antigen. 15 µg purified antigen per gel were boiled in reducing sample buffer (Laemmli, 1970) and applied to a 12%-SDS polyacrylamide mini gel (8.6 cm×7.7 cm×0.1 cm, Biometra). After electrophoretic separation at 25–30 mA, the proteins (antigen) were immobilized on a nitrocellulose by means of semi-dry blot technique.

The membrane was blocked with 2% skimmed-milk powder In PBS (30 min, room temperature) and washed three times for 5 min with TBS/Tween 20 (0.2%). For the following incubation step, the membrane was clamped in an Accutran cross blot screening unit (Schleicher and Schüll) using a grid plate with 34 cross channels. In each of the traces that were formed, 250 µl of TBS/Tween 20 and 250 µl of the hybridoma culture supernatants to be tested are added. Incubation was carried out while shaking for 2 h at room temperature.

After washing three times[1] TBS/Tween 20, the membrane was incubated for 1 h with the POD-conjugated secondary antibody (rabbit-anti-mouse Ig-POD, DAKO). The membrane was washed three times and the immune complex was visualised by adding the 3,3-diaminobenzidine substrate solution (DAB, Sigma). The protein bands binding the antibodies were subsequently visualized by an insoluble peroxidase substrate.

[1]Translator's note: word missing. Should probably read: "with"

6 hybridoma culture supernatants exhibited a band that corresponds to the catalase (58 kDa), 3 were negative in Western blot, however, showed a positive reaction with native antigen in ELISA. They are likely to recognize a conformation epitope. Table 2 shows a summary of the results.

EXAMPLE 6

Screening of mAk Culture Supernatants in Patients' Samples (Mixed Polyclonal/Monoclonal System)

TABLE 1

HP25.2m/2H10: sensitivity und specificity in the sandwich ELISA using patients' samples

| stool sample | patient's infection status | catching-ab: pab against HP detection-AK: HP25.2m/ 2H10 (culture supernatant) $OD_{450-620}$ | analysis cut off: 0.1: $OD_{450-620} = 0.1$ |
|---|---|---|---|
| CX0010 | POSITIVE | 0.25 | positive |
| CX1014 | POSITIVE | 0.75 | positive |
| CX1029 | POSITIVE | 0.18 | positive |
| CX1038 | POSITIVE | 0.09 | negative |
| CX1052 | POSITIVE | 0.11 | positive |
| CX2008 | POSITIVE | 0.63 | positive |
| CX2009 | POSITIVE | 0.32 | positive |
| CX2016 | POSITIVE | 0.07 | negative |
| CX2019 | POSITIVE | 0.59 | positive |
| CX2029 | POSITIVE | 0.52 | positive |
| CX0213 | POSITIVE | 0.04 | negative |
| CX294-1 | POSITIVE | 0.14 | positive |
| CX3098 | POSITIVE | 0.13 | positive |
| CX3146 | POSITIVE | 0.05 | negative |
| CX3148 | POSITIVE | 0.08 | negative |
| CX3234 | POSITIVE | 0.18 | positive |
| CX4003 | POSITIVE | 0.17 | positive |
| CX4006 | POSITIVE | 0.25 | positive |
| CXT001 | POSITIVE | 0.23 | positive |
| CXT002 | POSITIVE | 053 | positive |
| CXT003 | POSITIVE | 0.12 | positive |
| CXT004 | POSITIVE | 0.03 | negative |
| CXT005 | POSITIVE | 0.03 | negative |
| CXT006 | POSITIVE | 0.31 | positive |
| CXT007 | POSITIVE | 0.08 | negative |
| CXT008 | NEGATIVE | 0.29 | positive |
| CX1031 | NEGATIVE | 0.08 | negative |
| CX1049 | NEGATIVE | 0.7 | positive |
| CX1051 | NEGATIVE | 0.09 | negative |
| CX0142 | NEGATIVE | 0.03 | negative |
| CX0185 | NEGATIVE | 0.03 | negative |
| CX0189 | NEGATIVE | 0.08 | negative |
| CX0193 | NEGATIVE | 0.03 | negative |
| CX2010 | NEGATIVE | 0.08 | negative |
| CX2018 | NEGATIVE | 0.09 | negative |
| CX0220 | NEGATIVE | 0.03 | negative |
| CX0231 | NEGATIVE | 0.03 | negative |
| CX0258 | NEGATIVE | 0.02 | negative |
| CX3008 | NEGATIVE | 0.09 | positive |
| CX3011 | NEGATIVE | 0.08 | negative |
| CX3033 | NEGATIVE | 0.07 | negative |
| CX3035 | NEGATIVE | 0.09 | negative | ab: antibody; HP: *H. pylori*; pab polyclonal antibody

In the sandwich ELISA using patients' samples the monoclonal antibody HP25.2m/2Hallin (K10) showed a sensitivity of 68% (17 of 25 positive samples were recognized correctly) and a specificity of 82% (14 of 17 samples were recognized correctly)

TABLE 2

Characterization of the monoclonal antibodies against catalase

| fusion/clon | Isotyp | WB (Ag) | NWG (ng/ml) | stool samples recognized correctly pos. samples | neg. samples |
|---|---|---|---|---|---|
| HP25.2m/2H10 | IgG2a, κ | + | 1.5 | 17 of 25 | 14 of 17 |
| HP25.6m/1G4 | IgG1, κ | + | 1.5 | 4 of 5 | 2 of 2 |
| HP25.6m/1B5 | IgG1, κ | + | 3–6 | 3 of 5 | 2 of 2 |
| HP25.6m/1H4 | IgG1, κ | + | 3–6 | 2 of 5 | 2 of 2 |
| HP25.6m/4E3 | IgG1, κ | + | 6 | 2 of 5 | 2 of 2 |
| HP25.6m/1A5 | IgG1, κ | + | 6 | 2 of 5 | 2 of 2 |
| HP25.6m/5E4 | IgG1, κ | − | 1.5 | 1 of 5 | 2 of 2 |
| HP25.6m/4A12 | IgG1, κ | − | 1.5 | 1 of 5 | 2 of 2 |
| HP25.6m/5F4 | IgG1, κ | − | 1.5 | 1 of 5 | 2 of 2 |

Ag: antigen; WB: Western blot; NWG: detection limit

Results

Table 2 summarizes the results of the isotype determination, the Western blot analyses, the determination of the detection limit and the patient recognition for the monoclonal antibodies in the culture supernatant against catalase. In the mixed polyclonal-monoclonal sandwich ELISA system, the mab HP25.2m/2Hallin (K10) shows a sensitivity of 68% and a specificity of 82%. An improvement of sensitivity and specificity was shown when purified mab (instead of culture supernatant) was used in a purely monoclonal ELISA system.

For this purpose, either a monoclonal antibody may be used which is directed against the same epitope or two different monoclonal antibodies which are directed against different epitopes of the same antigen (cf. Example 8) as catching and detecting antibodies.

EXAMPLE 7

Purification of Monoclonal Antibodies from Hybridoma Culture Supernatants

The purification of mab from serum-free hybridoma culture supernatants was carried out by means of a modified protein-G affinity chromatography (Pharmacia Biotech, 1994).

The filtered (0.45 μm) culture supernatants were conducted directly over a protein G matrix. The detection of the protein in the flow through or in the eluate was carried out via measuring the optical density at 280 nm. After washing with 150 mM PBS, pH 7.2, until the detector background value, elution was conducted with 0.1 M glycine/HCl, pH 3.3. The protein matrix was regenerated with 0.1 M glycine/HCl, pH 2.7.

EXAMPLE 8

Characterisation of the Purified Monoclonal Antibodies and Selection of the Antibodies for the Test The antibodies showing the best detection properties for stool sample recognition during measurement from the culture supernatant were further characterized in purified state. First, the affinity constants were determined by means of surface plasmon resonance. Further, the binding regions of the antibodies were mapped (epitope mapping). Finally, suitable pairings of antibodies were selected by means of stool samples in the sandwich stool ELISA and in the rapid test.

Characterization of Antibody-Antigen Interactions by Means of Surface Plasmon Resonance Spectroscopy (SPR Spectroscopy)

By means of SPR spectroscopy, it is possible to determine the affinity constants of the monoclonal antibodies. Thus, suitable antibodies for the development of ELISA and quick tests can be found.

Conduction of the Surface Plasmon Resonance Spectroscopy on the Pharmacia BIAcore All steps were carried out on a Pharmacia Biacore Processing Unit CA 186 according to the manufacturer's instructions (BIAcore Methods Manual).

Catalase was Immobilized through amine coupling on the dextrane matrix of the BIAcore CM5 sensor chip. For the activation of the dextrane matrix 45 μl of a 1:1-mixture of 0.05 M N-hydroxysuccinimide (NHS) and 0.2 M 1-ethyl-3-3-dimethylaminopropyl)carbodiimide (EDC) solution was conducted over the sensor chip at a flow rate of 5 μl/min. Then, the catalase (35 μl; 50 μg/ml in 10 mM sodium acetate, pH 5.0) were bound to the dextrane matrix. The remaining NHS ester was deactivated with 1 M ethanolamine (35 μl). Catalase that was not covalently bound to the dextrane matrix was removed by regenerating the sensor chip with HCl (10 mM; 15 μl).

By adding the catalase-specific monoclonal antibodies, these were made react with immobilized catalase and the mass attachment to the detector was measured. Antibody solutions in different concentrations ranging from 20 to 670 nM were used. They were injected via the catalase immobilized on the sensor chip at a flow rate of 25 μl/min each.

The values for the rate constants of the adsorption ($k_{on}$) and desorption ($k_{off}$) of the antibody could be calculated (BIAevaluation software 3.0). 4 of the 6 monoclonal antibodies tested showed very good affinites $K_D$>5E-10 (Table 3).

TABLE 3

Results of the affinity determination of the monoclonal antibodies against catalase

| Mab | $K_{on}$ [$M^{-1} s^{-1}$] | $K_{off}$ [$s^{-1}$] | $K_D$ [M] |
|---|---|---|---|
| HP25.2m/2H10 | 1.44E+05 | 3.90E−05 | 2.71E−10 |
| HP25.6/1G4 | 1.41E+05 | 2.52E−05 | 1.79E−10 |
| HP25.6m/1H4 | 7.12E+04 | 4.12E−05 | 5.79E−10 |
| HP25.6m/1B5 | 5.67E+04 | 3.86E−05 | 6.81E−10 |
| HP25.6m/4E3 | 4.92E+04 | 5.96E−05 | 1.21E−09 |
| HP25.6m/1A5 | 3.91E+04 | 4.77E−05 | 1.22E−09 |

$K_D = k_{off} : = k_{on}$

Epitope Mapping of the Monoclonal Antibodies Against Catalase

The epitope mapping was carried out by Pepscan Systems (Netherlands). A peptide bank (30-mere with an overlap of 27 amino acids) of the catalase was produced on plastic maps and incubated with the antibodies. The determined epitopes (peptides to which antibodies had bound) are listed in Table 4. HP25.2m/2H10 (K10) exhibited unspecific peptide recognition, i.e. this antibody is very likely to bind to a discontinuing structure epitope. Apart from the main recognition region (cf. Table 4), HP25.6m/1B5 also exhibited further unspecific peptide bonds which give reason for the expectation that a structure component is involved. When transferring the detected epitopes to the structure of the *E. coli* catalase (Bravo et al., 1999) it becomes evident that the antibodies HP25.6m/1B5, 1A5 4E3, 1G4 and 1H4 bind in the enzyme centre (amino acid 190–360), a region which is near the catalytic domaine.

TABLE 4

Results of the epitope mapping of the catalase-mab

| Mab | recognized eptiope |
|---|---|
| HP25.2m/2H10 | discontinuing |
| HP25.6m/1B5 | EGNWDLVGNNTPVFFIRDAIKFPDFIHTQKRDPQTN |
| HP25.6m/4E3 | IARGDYPKWLSTQVMPEEDAKKYRFHPFDVTK |
| HP25.6m/1A5 | IARGDYPKWLSTQVMPEEDAKKYRFHPFDVTK |
| HP25.6m/1H4 | SRGDYMQNGYYGSLQNYTPSSLPGYKEDKS |
| HP25.6m/1G4 | 1. EEAAEIRKHDPDSNQRDLFDAIARGDYPKW |
|  | 2. DDSDYYTQPGDYYRSLPADEKERLHDT |
|  | ERLHDTIGESLAHYTHKAEIVDKQLEHFKKA |

Overlapping recognition regions of the antibodies are underlined.

Determination of Suitable Antibody Pairings by Means of Patients' Stool

First, the antibodies against catalase were tittered against each other. Then, the patients' stool samples were tested by means of the ELISA systems optimized in said manner and the detection limits of catalase were determined in human zero stool (Table 5).

Set-Up of the Sandwich ELISA:

The coating of the ELISA plates (MaxiSorb; Nunc) was carried out at 37° C. for one hour with 100 µl of an mab solution in carbonate buffer, 0.1 M, pH 9.5. For blockage of the binding sites still free 200 µl 150 mM PBS were pipetted with 0.2% fish gelatine (w/v) per dish and incubated for 30 min at room temperature. Subsequently, they were washed twice with 250 µl washing buffer 1 (PBS with 0.025% Tween). Human stool was suspended with 150 mM PBS at a ratio of 1:10 (w/v) adding 2% skimmed milk powder and 1 mM EDTA. For the determination of the antigen detection limit purified *H. pylori* catalase was added to the stool suspension of an *H. pylori* negative patient (zero stool) at known concentrations. The stool sample suspensions were centrifuged at 7000 g for 5 min. Per dish 100 µl of the supernatant each were incubated for 1 hour. The samples were applied as double values. Subsequently, the plate was washed four times with washing buffer 2 (250 µl PBS adding 0.2% Tween). Then, 100 µl of a solution of biotin-coupled [ . . . ][2] in PBS, 0.1% BSA, were added and incubated at room temperature for 60 min. The detection of the bound antigen/antibody complexes was carried out by adding a conjugate of streptavidin with POD (Dianova). Then, the POD turns the colourless substrate TMB (Sigma) into a blue product in the following step. After 5 to 10 minutes, or as soon as the negative control showed a slight blue colouring, the reaction was stopped by adding 1 N sulphuric acid (100 µl/dish). The intensity of the colour reaction was measured in the ELISA reader (MWG Spektral). The measurement was carried out at 455 nm against the reference wavelength of 620 nm.

[2]Translator's note: word missing; should probably read: "antibodies"

HP25.2m/2H10 (Table 5) proved to be a suitable detector antibody for the combination with all the other antibodies tested. Due to the affinity data, HP25.6m/1B5, 1 G4 and 1 H4 were tested as catching antibodies in the rapid test. HP25.6m/1B5 proved to be the best catching antibody.

TABLE 5

Results of the finding of the pairings of the monoclonal antibodies against catalase

| Biotinylated detecting antibody | | catching antibodies | | | |
|---|---|---|---|---|---|
|  |  | 25.2m/2H10 | 25.6m/1B5 | 25.6m/1G4 | 25.6m/1A5 | 25.6m/1H4 |
| 25.2m/2H10 | N:003 |  | 0.1 | 0.03 | 0.1 | 003 |
|  | G4:7–8 |  | 7 | 8 | 7 | 8 |
|  | G0:2 |  | 2 | 2 | 2 | 2 |
| 256m/185 | N:0, 1 | 0.1 |  | 0.1 | 0.03 | 0.3 |
|  | G4:8 | 7 |  | 5 | 7 | 8 |
|  | G0:2 | 1 |  | 2 | 2 | 2 |
| 25.6m/1G4 | N:0.3 | 0.1 | 0.1 |  | 0.01 | 0.1 |
|  | G4:6–8 | 7 | 8 |  | 8 | 8 |
|  | G0:1–2 | 2 | 4 |  | 2 | 2 |
| 25.6m/1A5 | N:0.3 | 011 | 0.3 | 0.1 |  | 0.3 |
|  | 04:6–7 | 7 | 5 | 7 |  | 8 |
|  | G0:2 | 2 | 2 | 2 |  | 2 |
| 25.6m/1H4 | N:0.1 | 0.3 | 0.1 | 0.3 | 0.1 |  |
|  | 04:8 |  | 4–7 | 7 | 8 |  |
|  | G0:3 |  | 2 | 2 | 2 |  |

Patient recognition (detection of 8 critical G4 and 4 G0 patients' samples)
N = detection limits [ng/ml] of the catalase in zero stool
Critically positive = samples whose detection has proven to be particularly

EXAMPLE 9

Production of Conjugates for use in Immunochromatographic Rapid Tests

Coupling of mab with Biotin

After purification, the monoclonal antibodies are coupled with biotin. Coupling was carried out according to known methods (Harlow & Lane, 1988).

The monoclonal antibodies were conjugated at a concentration of approx. 1–2 mg/ml. Before coupling, the antibodies were rebuffered by dialysis in 0.1 M sodium acetate buffer, pH 8.3, and 0.1 M sodium hydrogen carbonate buffer, pH 8.3. For each 1 mg of antibodies 50 µg N-hydroxysuccinimidobiotin (NHS-d-biotin; Sigma) was added and mixed in DMSO. The mixture was incubated for one hour at room temperature. Then, the biotinylated antibodies were freed from uncoupled NHS-d-biotin by extensive dialysis against 0.15 M PBS, 0.05% $NaN_3$, pH 7.5.

Coupling of mab to Colloidal Gold

The monoclonal antibodies (mab) were coupled to colloidal gold according to standard methods (Frens, 1973; Geoghegan and Ackerman, 1977; Slot et al., 1985). Gold colloid with a particle size of 40 nm, Opposition Division (520) nm=1 (British BioCell, Cardiff, England) was adjusted with 0.1 M K2CO3 to pH 9. Purified mab was dialysed against 2 mM borate buffer, pH 9.2, and diluted to a concentration of 0.1 mg/ml. For the coupling 2 ml of the mab solution were added in drops to 20 ml of the gold solution while stirring quickly and incubated for 30 min at room temperature. The optimal lgG concentration and the suitable pH value for the coupling were determined for each mab individually. For the stabilization of the gold lgG conjugate, 2 ml bovine serum albumin was added at a concentration of 10% and incubated for another 5 min. Subsequently, gold colloid not coupled with lgG and free lgG were separated by centrifugation. For this purpose, the coupling preparation was centrifuged at 15000 rpm (Sorvall, SS-34) for 30 minutes and the clear supernatant was sucked off by means of vacuum. The gold lgG conjugate deposited at the bottom of the centrifugation tube as loose sediment dyed dark red was absorbed into 2 ml 20 mM Tris, pH 8.2, adding 1% bovine serum albumin and 0.05% $NaN_3$.

EXAMPLE 10

Immunochromatographic Rapid Test

An immunochromatographic test according to the sandwich principle was set up with the antibody pair HP25.2m/2H10 and HP25.6m1/1B5. As schematically illustrated in FIGS. 9 and 10, this test consists of a sample application area (1), a filter (2), a test or analysis area (3) and an absorption area (4).

The purified mab HP25.2m/2H10 was coupled to gold (British BioCell, Cardiff, England) as signal-forming immune reagent. The mab gold conjugate was diluted in deionised water by adding 5% sucrose (Sigma, Deisenhofen) to an OD (520 nm) from 3 and applied to a conjugate fleece from glass fiber (Pall, Dreieich). Subsequently, the conjugate fleece was vacuum dried.

As testing area (FIG. 10, 3) nitrocellulose with a flow rate of 95–175 sec/4 cm (Millipore, Bedford, Mass., USA) was coated with the immune reagents which form the test and control line. For this purpose, a specific application appliance for test strips (Imagene, Hanover, N.H., USA) was used. As test line (FIG. 10, 6) purified mab HP25.6m/1B5 was applied in phosphate buffer pH, 7.4, at a concentration of 1–2 µg/cm. As control line (FIG. 10, 7), a polyclonal anti-mouse antibody (Dianova, Hamburg) was applied at a concentration of 0.1–0.3 µg/cm.

Subsequently, the coated nitrocellulose and the coated conjugate fleece were stuck to polyester carriers with the other components of the test strip (G&L, Santa Clara, Calif., USA) and cut into single strips with a width of 5 mm. As filter (FIG. 10, 2) glass fiber materials (Ahlstrom, Mt. Holly Springs, Pa., USA; Pall, Dreieich; Whatman, Maidstone, England) were used in a width of 1–2 cm. For the absorption area (FIG. 10, 4) absorbent cellulose or cellulose glass-fiber materials were used in a width of 2–3 cm (Pall, Dreireich; Schleicher & Schuell, Dassel; Whatman, Maidstone, England).

EXAMPLE 11

Immunochromatographic Rapid Test Using Streptavidin as Test Line

Unlike the rapid test described in Example 10, the mab HP25.6m/1B5 used as test line was coupled to biotin and dried onto a second conjugate fleece of the sample application area. As test line recombinant streptavidin (Roche, Mannheim) was coated at a concentration of 10–20 mg/ml in phosphate buffer, pH, 7.4.

In this sandwich set-up both antibody conjugates are mobile during the test and migrate across the test strip during the test. In the presence of antigens, the complete sandwich complex, which is stopped at the test line due to the binding of biotin to streptavidin, is formed during migration.

EXAMPLE 12

Detection of *H. pylori* in Human Stool by Means of Immunochromatographic Rapid Test Patients' Samples For the evaluation of the immunochromatographic rapid test, 200 stool samples from patients of ten different hospitals or gastroenterological surgeries were at disposal. The samples were both from patients who did not have any troubles with or diseases of the gastrointestinal tract and from patients who underwent treatment due to troubles with or diseases of the gastrointestinal tract. The infection status of the patients negative was determined by means of $^{13}$C-urea breath test and/or histological analyses of gastric biopsies. Patients exhibiting contradicting results in these two methods accepted as gold standard were not included in the evaluation. The stool samples to be tested were codified so that the laboratory staff did not know about the infection status.

Carrying Out the Test

For the rapid tests, the stool samples were dissolved at a ratio of 1:15 in a sample buffer and 500 µl of the sample solution was applied to the application area (sample application area) of the test strip. After 15 minutes, the test was analysed visually. The test signal at the test line was rated present (test result positive) or not present (test result negative). The reading of the test results was carried out independently each by three persons who had no qualification as laboratory personnel. In addition, the tests were evaluated by the laboratory personnel semi-quantitatively with 0 (negative), 1 (slightly positive) and 2 (strongly positive).

Table 6 shows the results achieved by the stool rapid tests, compared to the two reference methods, after evaluation of 200 patients' samples in total. In the test, 95 of the all in all 100 *H. pylori* positive samples were found to be true positive, 5 samples showed a false negative result. 94 samples of the all in all 100 *H. pylori* negative samples were found to be true negative, 6 samples showed a false positive result. In comparison with, sensitivity and specificity of the rapid test were 95% and 94%.

TABLE 6

Test results of the gold standard method and of the rapid test (semi-quantitatively) of the evaluation of all in all 200 stool sample

| sample number | breath test | gastric biopsy | rapid test |
|---|---|---|---|
| 1001 | n.d. | negative | 0 |
| 1002 | n.d. | negative | 0 |
| 1007 | n.d. | negative | 0 |
| 1008 | n.d. | negative | 0 |
| 1010 | n.d. | negative | 0 |
| 1012 | n.d. | negative | 0 |
| 1017 | n.d. | negative | 0 |
| 1021 | n.d. | negative | 0 |
| 1022 | n.d. | negative | 0 |
| 1024 | n.d. | negative | 0 |
| 1025 | n.d. | negative | 0 |
| 1027 | n.d. | negative | 0 |
| 1030 | n.d. | negative | 0 |
| 1031 | n.d. | negative | 0 |
| 1032 | n.d. | negative | 0 |
| 1034 | n.d. | negative | 0 |
| 1035 | n.d. | negative | 0 |
| 1040 | n.d. | negative | 0 |
| 1046 | n.d. | negative | 0 |
| 2002 | n.d. | negative | 0 |
| 2006 | n.d. | negative | 0 |
| 2007 | negative | n.d. | 0 |
| 2010 | n.d. | negative | 0 |
| 2012 | negative | n.d. | 0 |
| 2013 | negative | n.d. | 0 |
| 2014 | negative | n.d. | 0 |
| 2015 | n.d. | negative | 1 |
| 2017 | negative | negative | 0 |
| 2018 | negative | negative | 0 |
| 2023 | n.d. | negative | 0 |
| 2024 | negative | n.d. | 0 |
| 2028 | n.d. | negative | 0 |
| 2033 | negative | negative | 0 |
| 2034 | negative | negative | 0 |
| 2043 | n.d. | negative | 0 |
| 3123 | negative | n.d. | 0 |
| 3213 | n.d. | negative | 0 |
| 3224 | negative | n.d. | 0 |
| 3225 | n.d. | negative | 0 |
| 4004 | n.d. | negative | 0 |
| 5004 | n.d. | negative | 0 |
| 5007 | n.d. | negative | 0 |
| 5008 | n.d. | negative | 0 |
| 5009 | n.d. | negative | 0 |
| 5010 | n.d. | negative | 0 |
| 5012 | n.d. | negative | 0 |
| 5013 | n.d. | negative | 0 |
| 5017 | n.d. | negative | 0 |
| 5018 | n.d | negative | 0 |
| 5019 | n.d. | negative | 0 |
| 5020 | n.d. | negative | 0 |
| 5021 | n.d. | negative | 0 |
| 5022 | n.d. | negative | 0 |
| 5024 | n.d. | negative | 0 |
| 5025 | n.d. | negative | 0 |
| 5027 | n.d. | negative | 0 |
| 5028 | n.d. | negative | 0 |
| 5030 | n.d. | negative | 0 |
| 5031 | n.d. | negative | 2 |
| 5033 | n.d. | negative | 0 |
| 5035 | n.d. | negative | 0 |
| 5036 | n.d. | negative | 0 |
| 5040 | n.d. | negative | 0 |
| 5042 | n.d. | negative | 0 |
| 5046 | n.d. | negative | 0 |
| 5052 | n.d. | negative | 0 |
| 5056 | n.d. | negative | 1 |
| 5057 | n.d. | negative | 0 |
| 5060 | nd. | negative | 1 |
| 5063 | n.d. | negative | 0 |
| 5064 | n.d. | negative | 0 |
| 5066 | n.d. | negative | 0 |
| 5067 | n.d. | negative | 0 |
| 5068 | n.d. | negative | 0 |
| 6002 | n.d. | negative | 0 |
| 6005 | n.d. | negative | 0 |
| 6008 | n.d. | negative | 0 |
| 6009 | n.d. | negative | 0 |
| 6017 | n.d. | negative | 0 |
| 6019 | n.d. | negative | 0 |
| 6024 | n.d. | negative | 0 |
| 6026 | n.d. | negative | 0 |
| 6029 | n.d. | negative | 0 |
| 6033 | n.d. | negative | 0 |
| 6038 | n.d. | negative | 0 |
| 6039 | n.d. | negative | 0 |
| 7005 | n.d. | negative | 0 |
| 7006 | n.d. | negative | 2 |
| 7009 | n.d. | negative | 0 |
| 7013 | n.d. | negative | 0 |
| 8004 | n.d. | negative | 0 |
| 8047 | n.d. | negative | 0 |
| 9004 | n.d. | negative | 0 |
| 9005 | n.d. | negative | 0 |
| 9010 | n.d. | negative | 0 |
| 9011 | n.d. | negative | 0 |
| 9012 | n.d. | negative | 0 |
| 9013 | n.d. | negative | 0 |
| 9015 | n.d. | negative | 1 |
| 9019 | n.d. | negative | 0 |
| 213 | n.d. | positive | 1 |
| 444 | n.d. | positive | 1 |
| 1003 | n.d. | positive | 1 |
| 1013 | n.d. | positive | 2 |
| 1014 | n.d. | positive | 1 |
| 1015 | n.d. | positive | 2 |
| 1028 | n.d. | positive | 1 |
| 1029 | n.d. | positive | 2 |
| 1037 | n.d. | positive | 1 |
| 2005 | positive | n.d. | 2 |
| 2008 | n.d. | positive | 2 |
| 2009 | positive | n.d. | 2 |
| 2016 | n.d. | positive | 2 |
| 2029 | positive | positive | 2 |
| 2032 | positive | positive | 2 |
| 2035 | n.d. | positive | 2 |
| 2039 | positive | positive | 2 |
| 2040 | nd. | positive | 2 |
| 2041 | positive | positive | 2 |
| 2042 | positive | positive | 2 |
| 3146 | positive | n.d. | 2 |
| 3219 | positive | positive | 2 |
| 3220 | positive | positive | 2 |
| 3231 | positive | positive | 2 |
| 3234 | positive | positive | 2 |
| 3241 | positive | positive | 1 |
| 3570 | positive | n.d. | 2 |
| 4003 | n.d. | positive | 2 |
| 4005 | positive | positive | 1 |
| 4006 | n.d. | positive | 2 |
| 4018 | n.d. | positive | 2 |
| 4019 | n.d. | positive | 2 |
| 4020 | n.d. | positive | 2 |
| 5001 | n.d. | positive | 2 |
| 5006 | n.d. | positive | 2 |
| 5029 | n.d. | positive | 2 |
| 5039 | n.d. | positive | 2 |
| 5048 | n.d. | positive | 2 |
| 5050 | n.d. | positive | 1 |
| 5053 | n.d. | positive | 2 |
| 5055 | n.d. | positive | 2 |
| 5058 | n.d. | positive | 2 |
| 5061 | n.d. | positive | 2 |
| 5069 | n.d. | positive | 1 |

TABLE 6-continued

Test results of the gold standard method and of the rapid test
(semi-quantitatively) of the evaluation of all in all 200 stool sample

| sample number | breath test | gastric biopsy | rapid test |
|---|---|---|---|
| 5072 | n.d. | positive | 2 |
| 5075 | n.d. | positive | 2 |
| 5076 | n.d. | positive | 2 |
| 5078 | n.d. | positive | 2 |
| 5090 | n.d. | positive | 2 |
| 5092 | n.d. | positive | 2 |
| 5100 | n.d. | positive | 2 |
| 5150 | n.d. | positive | 0 |
| 6001 | n.d. | positive | 2 |
| 6004 | n.d. | positive | 2 |
| 6013 | n.d. | positive | 1 |
| 6014 | n.d. | positive | 2 |
| 6015 | n.d. | positive | 2 |
| 6018 | n.d. | positive | 2 |
| 6020 | n.d. | positive | 1 |
| 6022 | n.d. | positive | 2 |
| 6027 | n.d. | positive | 2 |
| 6040 | n.d. | positive | 2 |
| 6050 | n.d. | positive | 2 |
| 6052 | n.d. | positive | 2 |
| 6064 | n.d. | positive | 2 |
| 6065 | n.d. | positive | 2 |
| 7001 | n.d. | positive | 1 |
| 7002 | n.d. | positive | 2 |
| 7003 | n.d. | positive | 1 |
| 7020 | n.d. | positive | 0 |
| 8026 | n.d. | positive | 0 |
| 8033 | n.d. | positive | 2 |
| 9001 | n.d. | positive | 2 |
| 9002 | n.d. | positive | 2 |
| 9003 | n.d. | positive | 2 |
| 9006 | n.d. | positive | 2 |
| 9007 | n.d. | positive | 1 |
| 9008 | n.d. | positive | 2 |
| 9009 | n.d. | positive | 0 |
| 9014 | n.d. | positive | 2 |
| 9017 | n.d. | positive | 2 |
| 9018 | n.d. | positive | 2 |
| 9022 | n.d. | positive | 2 |
| T 01 | positive | n.d. | 2 |
| T 02 | positive | n.d. | 2 |
| T 03 | positive | positive | 2 |
| T 04 | positive | positive | 1 |
| T 05 | positive | positive | 1 |
| T 07 | positive | positive | 1 |
| T 09 | positive | n.d. | 2 |
| T 10 | positive | n.d. | 1 |
| T 13 | n.d. | positive | 2 |
| T 53 | positive | n.d. | 2 |
| T 58 | positive | n.d. | 1 |
| T 64 | positive | n.d. | 2 |
| T 67 | positive | n.d. | 1 |
| T 68 | positive | n.d. | 2 |
| T 70 | positive | n.d. | 1 |
| T 77 | positive | n.d. | 0 |
| T 88 | positive | n.d. | 2 | n.d.: not determined; 0: negative; 1: slightly positive; 2: strongly positive (n = 200)

| Method | gold standard | |
|---|---|---|
| | positive | negative |
| H. pylori-rapid test positive | 95 | 6 |
| negative | 5 | 94 | sensitivity: 95%
Specificity: 94%

EXAMPLE 13

Cloning and Sequence Determination of the Functional Variable Regions of Immunoglobulins from Hybridoma Cell Lines Total RNA was isolated from antibody-producing hybridoma cell lines according to ChomczynskJ (Chomczynski, 1987).

Then, the corresponding cDNA was synthesized according to standard methods (Sambrook et al., 1989).

The DNA regions encoding the kappa light chain as well as the heavy chain Fd segment (VH or CH1) of the respective antibodies were amplified by means of PCR. The oligonucleotide primer set stated in Table 7 was used, the cDNA isolated from the single hybridoma cell lines served as a template.

The primer set used leads to a 5'-Xhol and a 3'-Spel cleavage site in the heavy chain Fd fragments as well as to a 5'-Sacl and a 3'-Xbal cleavage site in the kappa light chains. For the PCR amplification of the DNA fragments encoding the heavy chain Fd 11 different 5'-VH primers (MVH 1-8 and MULH 1-3) were each combined with the 3'VH primer MlgGZa (HP25.2m/2H10) or the 3'-VH primer MlgGl (HP25.6 m/1B5).

For the amplification of the DNA fragments which encode the kappa light chains, 11 different 5'-VK primers (MUVK 1-7 and MULK 1-4) were each combined with the 3'-VK primer 3'MUCK.

The following temperature program was used in all PCR amplifications: denaturation at 94° C. for 30 s, primer attachment at 52° C. for 60 s, polymerization at 72° C. for 90 s. This program was maintained for 40 cycles, followed by a final completion of the fragments at 72° C. for 10 min.

The results of the PCR amplifications were separated by means of agarose gel electrophoresis and the DNA bands of the expected molecular weight were isolated. For the antibody 25.2m/2H10, the isolated bands were then subjected to a restriction digestion using the enzymes Xhol and Spel (heavy chains) or Sacl and Xbal (light chains). The fragments obtained were cloned into the plasmid vector Bluescript KS (Stratagene) after the vector had first been cleaved with the restriction enzymes Xhol and Spel or Sacl and Xbal.

Subsequently, plasmid preparations of the cloned heavy and light chain fragments were sequenced. Sequences were chosen which encode the functional variable regions of the heavy and light chains of immunoglobulin (VH or VL). In this way, it was possible to identify exactly one functional VH and one functional VL region for each hybridoma cell line. FIG. 1 and FIG. 2 show the functional VH and VL sequences. The first four amino acids of the VH region were completed by recloning. Cloning and sequencing were carried out according to standard methods (Sambrook et al., 1989).

For the antibody 25.6m/1B5, the isolated bands were then directly sequenced and a functional light chain and a functional heavy chain were identified. The heavy chain Fd fragment and the light chain were then subjected to a restriction digest using the enzymes Xhol and Spel (heavy chain) and Sacl and Xbal (light chain). After the plasmid vector pBSIIIHisEx (Connex) had been split by means of the restriction enzymes Xho I and Spe I and/or Sac I and Xba I, the obtained fragments were cloned into this vector and sequenced again.

In this way, exactly one functional VH and one functional VL area could be identified for this hybridoma cell line. The functional VH and VL sequences are given in FIG. 3/FIG. 4. In the VH and VL sequences, the mature N-terminals are shown as they were determined by the sequencing by means of leader primer. Cloning and sequencing were carried out according to standard methods (Sambrook et al., 1989).

TABLE 7

List of the primers used for the PCR amplification of the functional variable regions of heavy and light immunoglobulin-chains (orientation 5'-3')

| | | |
|---|---|---|
| MVH1 | (GC)AG GTG CAG CTC GAG GAG TCA GGA CCT | (SEQ ID NO:58) |
| MVH2 | GAG GTC CAG CTC GAG CAG TCT GGA CCT | (SEQ ID NO:59) |
| MVH3 | CAG GTC CAA CTC GAG CAG CCT GGG GCT | (SEQ ID NO:60) |
| MVH4 | GAG GTT CAG CTC GAG CAG TCT GGG GCA | (SEQ ID NO:61) |
| MVH5 | GA(AG) GTG AAG CTC GAG GAG TCT GGA GGA | (SEQ ID NO:62) |
| MVH6 | GAG GTG AAG CTT CTC GAG TCT GGA GGT | (SEQ ID NO:63) |
| MVH7 | GAA GTG AAG CTC GAG GAG TCT GGG GGA | (SEQ ID NO:64) |
| MVH8 | GAG GTT CAG CTC GAG CAG TCT GGA GCT | (SEQ ID NO:65) |
| MULK1 | GGG GAG CTC CAC CAT GGA GAC AGA CAC ACT CCT GCT AT | (SEQ ID NO:66) |
| MULK2 | GGG GAG CTC CAC CAT GGA TTT TCA AGT GCA GAT TTT CAG | (SEQ ID NO:67) |
| MULK3 | GGG GAG CTC CAC CAT GGA GWC ACA KWC TCA GGT CTT TRT A | (SEQ ID NO:68) |
| MULK4 | GGG GAG CTC CAC CAT GKC CCC WRC TCA GYT YCT KGT | (SEQ ID NO:69) |
| MlgG1 | TAT GCA ACT AGT ACA ACC ACA ATC CCT GGG | (SEQ ID NO:70) |
| MlgG2 | GAG AGA GGG GTT CTG ACT AGT GGG CAC TCT GGG CTC | (SEQ ID NO:71) |
| MUVK1 | CCA GTT CCG AGC TCG TTG TGA CTC AGG ATT CT | (SEQ ID NO:72) |
| MUVK2 | CCA GTT CCG AGC TCG TGT TGA CGC AGC CGC CC | (SEQ ID NO:73) |
| MUVK3 | CCA GTT CCG AGC TCG TGC TCA CCC AGT CTC CA | (SEQ ID NO:74) |
| MUVK4 | CCA GTT CCG AGC TCC AGA TGA CCC AGT CTC CA | (SEQ ID NO:75) |
| MUVK5 | CCA GAT GTG AGC TCG TGA TGA CCC AGA CTC CA | (SEQ ID NO:76) |
| MUVK6 | CCA GAT GTG AGC TCG TCA TGA CCC AGT CTC CA | (SEQ ID NO:77) |
| MUVK7 | CCA GTT CCG AGC TCG TGA TGA CAC AGT CTC CA | (SEQ ID NO:78) |
| MULH1 | GGG CTC GAG CAC CAT GGR ATG SAG CTG KGT MAT SCT CTT | (SEQ ID NO:79) |
| MULH2 | GGG CTC GAG CAC CAT GRA CTT CGG GYT GAG CTK GGT TTT | (SEQ ID NO:80) |
| MULH3 | GGG CTC GAG CAC CAT GGC TGT CTT GGG GCT GCT CTT CT | (SEQ ID NO:81) |
| 3'MUCK | GCG CCG TCT AGA ATT AAC ACT CAT TCC TGT TGA A | (SEQ ID NO:82) |

The invention claimed is:

1. A method for detecting an infection of a mammal with an acid-resistant microorganism belonging to the genus *Helicobacter* comprising:
   (a) provision of an immunochromatographic rapid test with a sample application area for the application of a stool sample of the mammal with an antigen and application of the stool sample,
   (b) incubation of the stool sample using (i) a first receptor under conditions permitting a complex formation of the antigen from the acid resistant microorganism with the receptor; or (ii) at least one of two different first receptors under conditions permitting a complex formation of the antigen from the acid-resistant microorganism with the at least one of two different first receptors and wherein the first receptor according to (i) or the at least one of two different first receptors according to (ii) specifically bind(s) to an epitope of an antigen which shows, at least with some mammals, a structure after passage through the intestine that corresponds to the native structure or the structure against which a mammal produces antibodies against after being infected or immunized with the acid-resistant microorganism or an extract or lysate thereof or a protein therefrom or a fragment thereof or a synthetic peptide and wherein said epitope is an epitope of an antigen selected from the group consisting of a catalase, urease and metalloproteinase; and
   (c) provision of a second receptor immobilized at an analysis area, wherein the second receptor binds an antigen receptor complex according to (b), and transport and detection of the formation of at least one antigen receptor complex according to (b) by accumulation of the antigen receptor complex at the second receptor in the analysis area.

2. The method according to claim 1, wherein the stool sample is suspended before the application.

3. The method according to claim 1, wherein a test strip is provided with an analysis area consisting of a cellulose or a cellulose derivative and the carrier material is suitable for the transport to take place via the capillary forces in the carrier material.

4. The method according to claim 1, wherein the first receptor(s) is/are immobilized and/or dried onto the test strip, soluble by the suspension, and/or the second receptor is/are immobilized and/or dried onto the test strip, insoluble by the suspension.

5. The method according to claim 1, wherein the step of resuspending the stool sample in a sample buffer is carried out with the stool sample before the incubation with the antibodies, said stool sample and sample buffer being in a ratio of 1:3 to 1:25.

6. The method according to claim 1, wherein antibodies or antibody conjugates are provided as first and/or second receptor(s).

7. The method of according to claim 1, wherein the first receptor in (i) or the at least one of two different first receptors in (ii) is labelled with visible coloured particles, the size of which ranges from 5 nm to 100 nm, or is labelled by means of a second receptor which specifically binds to the first receptor in (i), or at least one of two different first receptors in (ii), wherein the second receptor is labelled with visible or coloured particles the size of which ranges from 5 nm to 100 nm.

8. The method according to claim 7, wherein at least one of two different first receptors in case (ii) is not labelled with visible or coloured particles is conjugated with biotin and wherein the second receptor is streptavidin such that the first biotinylated receptor(s) is/are immobilised at the testing means by means of streptavidin.

9. The method according to claim 1, wherein the acid-resistant bacterium is *Helicobacter pylori* and wherein the antigen is a catalase.

10. The method according to claim 1, wherein the the first receptor in (i), or the at least one of two different first receptors in (ii) is an antibody, a fragment, a derivative or an aptamer.

11. The method according to claim 10, wherein a mixture of receptors is used for the detection, wherein the mixture of receptors has the function of catcher of the antigen, if the receptor is used as detector of the antigen and/or the mixture has the function of detector of the antigen, if the receptor is used as catcher of the antigen and the mixture of receptors is a polyclonal antiserum.

12. The method according to claim 10, wherein mixtures of receptors are used for the detection, wherein one mixture of receptors has the function of catcher of the antigen and another mixture has the function of detector of the antigen.

13. The method according to claim 10, wherein a mixture of receptors has the function of both catcher and detector of the antigen.

14. The method according to claim 12, wherein the polyclonal antiserum was produced against a lysate of the microorganism or wherein the polyclonal antiserum was produced against a purified or a (semi)synthetically-produced antigen.

15. The method according to any one of claims 12 to 14, wherein the receptor(s) which act(s) as catcher of the antigen (a) and/or the receptor(s) which act(s) as detector of the antigen (b) is/are replaced by an immune complex each, which, in case
   consists of at least one unlabelled antibody specifically binding the antigen and one labelled antibody specifically binding the at least one unlabelled antibody, which, in case
   consists of at least one non-immobilised antibody specifically binding the antigen and one antibody immobilised at the test line specifically binding this at least one non-immobilised antibody.

16. The method according to any one of claims 12 to 14, wherein the receptor and/or the mixture of receptors bind(s) (a) conformation epitope(s).

17. The method according to any one of claims 11 to 14, wherein the heavy chain of the antibody binding a catalase epitope exhibits at least one of the following CDRs:
   CDR1: SEQ ID NO.:9
   CDR2: SEQ ID NO.:10
   CDR3: SEQ ID NO.:11
   and wherein the DNA sequence encoding the heavy chain of the antibody exhibits at least one of the following CDRs:
   CDR1: SEQ ID NO.:12
   CDR2: SEQ ID NO.:13
   CDR3: SEQ ID NO.:14
   and wherein, the light chain of the antibody binding a catalase epitope exhibits at least one of the following CDRs:
   CDR1: SEQ ID NO.:15
   CDR2: SEQ ID NO.:16
   CDR3: SEQ ID NO.:17
   and wherein, the DNA sequence encoding the light chain of the antibody exhibits at least one of the following CDRs:
   CDR1: SEQ ID NO.:18
   CDR2: SEQ ID NO.:19
   CDR3: SEQ ID NO.:20.

18. The method according to any one of claims 11 to 14, wherein the heavy chain of the antibody binding a catalase epitope exhibits at least one of the following CDRs:
   CDR1: SEQ ID NO.:21
   CDR2: SEQ ID NO.:22
   CDR3: SEQ ID NO.:23
   and wherein the DNA sequence encoding the heavy chain of the antibody exhibits at least one of the following CDRs:
   CDR1: SEQ ID NO.:24
   CDR2: SEQ ID NO.:25
   CDR3: SEQ ID NO.:26
   and wherein, the light chain of the antibody binding a catalase epitope exhibits at least one of the following CDRs:
   CDR1: SEQ ID NO.:27
   CDR2: SEQ ID NO.:28
   CDR3: SEQ ID NO.:29
   and wherein the DNA sequence encoding the light chain of the antibody exhibits at least one of the following CDRs:
   CDR1: SEQ ID NO.:30
   CDR2: SEQ ID NO.:31
   CDR3: SEQ ID NO.:32.

19. The method according to any one of the claims 10 to 14, wherein the heavy chain of the antibody binding an epitope of the β-urease exhibits at least one of the following CDRs:
   CDR1: SEQ ID NO.:33
   CDR2: SEQ ID NO.:34
   CDR3: SEQ ID NO.:35
   or
   CDR1: SEQ ID NO.:36
   CDR2: SEQ ID NO.:37
   CDR3: SEQ ID NO.:38.

20. The method according to claim 19, wherein the DNA sequence of the antibody encoding the heavy chain exhibits at least one of the following CDRs:
   CDR1: SEQ ID NO.:39
   CDR2: SEQ ID NO.:40
   CDR3: SEQ ID NO.:41
   or
   CDR1: SEQ ID NO.:42
   CDR2: SEQ ID NO.:43
   CDR3: SEQ ID NO.:44.

21. The method according to any one of claims 10 to 14, wherein the light chain of the antibody binding an epitope of the P-urease exhibits at least one of the following CDRs:
   CDR1: SEQ ID NO.:45
   CDR2: SEQ ID NO.:46
   CDR3: SEQ ID NO 47:
   or
   CDR1: SEQ ID NO.:48
   CDR2: SEQ ID NO.:49
   CDR3: SEQ ID NO.:50.

22. The method according to claim 21, wherein the DNA sequence of the antibody encoding the light chain exhibits at least one of the following CDRs:
   CDR1: SEQ ID NO.:51
   CDR2: SEQ ID NO.:52
   CDR3: SEQ ID NO.:53
   or
   CDR1: SEQ ID NO.:54
   CDR2: SEQ ID NO.:55
   CDR3: SEQ ID NO.:56.

23. The method according to claim 1, wherein said method is automated.

24. An immunochromatographic testing means for detecting an infection of an acid-resistant microorganism belonging to the genus *Helicobacter* in a mammal according to the method of claim 1, comprising:
- a sample application area for the application of a stool sample from the mammal,
- a device for the incubation of the stool sample using (i) a first receptor under conditions that allow a complex formation between the antigen from the acid resistant microorganism and the first receptor; or (ii) at least two different first receptors under conditions that allow a complex formation between the antigen from the acid-resistant microorganism and the at least two different first receptors, and wherein the first receptor according to (i) or the at least two different first receptors according to (ii) specifically bind(s) an epitope of an antigen which shows, at least with some mammals, a structure after passage through the intestine that corresponds to the native structure or the structure against which a mammal produces antibodies against after being infected or immunized with the acid-resistant microorganism or an extract or lysate thereof or a protein therefrom or a fragment thereof or a synthetic peptide,
- a second receptor immobilized at an analysis area, wherein the second receptor specifically binds an antigen-receptor complex according to (b) and
- a transport device transporting the antigen-receptor complex according to (b) to the analysis area with the immobilised second receptor for the formation-of an analyte-receptor complex.

25. The testing means according to claim 24, wherein a test strip is provided with an analysis area consisting of a cellulose or a cellulose derivative, said test strip having a carrier material suitable for the transport to take place via the capillary forces in the carrier material.

26. The testing means according to claim 24, wherein the sample application area has a conjugate fleece and a subsequent filter in the direction of transport which is suitable to filter the solid substance parts of the stool or stool suspension.

27. The testing means according to claim 26, wherein the filter exhibits an exclusion size of 1 to 2 μm.

28. The testing means according to claim 26, wherein the filter is produced from glass fibre and/or polyester glass fibre mixtures.

29. The testing means according to claim 25, wherein the test strip is fixed on a polyester carrier material.

30. The testing means according to claim 24, wherein antibodies or antibody conjugates are provided as first and/or second receptor(s).

31. The testing means according to claim 24, wherein the first receptor in (i) or the at least one of two different first receptors in (ii) is labelled with visible or coloured particles, the size of which ranges from 5 nm to 100 nm or is labelled by means of a second receptor, which specifically binds to the first receptor in (i) or to the at least one of two different first receptors in (ii), wherein the second receptor is labelled with visible or coloured particles, the size of which ranges from 5 nm to 100 nm.

32. The testing means according to claim 31, wherein the at least one of two different first receptors in (ii), which is not labelled with visible or coloured particles, is conjugated with biotin and wherein the second receptor is streptavidin, such that the first biotinylated receptor(s) is/are immobilised at the testing means line by means of streptavidin.

33. The testing means according to claim 24, wherein a control segment is formed in the direction of transport behind the test segment.

34. The testing means according to claim 25, wherein the test strip exhibits an absorption area at its end in the direction of transport.

35. The testing means according to claim 25, wherein the test strip has a width of 3 to 10 mm and a length of 50 to 100 mm.

36. The testing means according to claim 26, wherein the length of the conjugate fleece is 5 to 30 mm, the overlap of the conjugate fleece and filter in flow direction is 5 to 15 mm; and wherein in the use of two conjugate fleeces, the length of the first conjugate fleece is 25 mm, the overlap of the first and the second conjugate fleeces in flow direction is approximately 12.5 mm, the length of the second conjugate fleece is approximately 12.5 mm, the overlap of the second conjugate fleece and filter in flow direction is approximately 10 mm, the length of the testing means or analysis area is 10 to 30 mm, the width is approximately 5 mm and the overlap of testing means or analysis area and absorption area in flow direction is approximately 1 mm.

37. The testing means according to claim 24, wherein the acid-resistant bacterium is *Helicobacter pylori* and wherein the antigen is a catalase.

38. The testing means according to claim 24, wherein the receptor is selected from the group consisting of an antibody, a fragment, a derivative and an aptamer.

39. The testing means according to claim 37, wherein a mixture of receptors when used for detection, the mixture of receptors functions as a catcher of the antigen when the receptor is used as a detector of the antigen and/or the mixture of receptors functions as a detector of the antigen, when the receptor is used as a catcher of the antigen and wherein the mixture of receptors is a polyclonal antiserum.

40. The testing means according to claim 37, wherein mixtures of receptors when used for detection, one of the mixtures of receptors functions as the catcher of the antigen while another mixture of receptors functions as the detector of the antigen and and wherein one of the mixture of receptors is a polyclonal antiserum.

41. The testing means according to claim 37, wherein a mixture of receptors that serves as both a catcher and a detector of the antigen is a polyclonal serum.

42. The testing means according to claim 39, wherein the polyclonal antiserum was produced against a lysate of the microorganism and, the lysate is a lysate with enriched antigen, or wherein the polyclonal antiserum was produced against a purified or a (semi)synthetically-produced antigen.

43. The testing means according to any one of claims 39 to 42, wherein the receptor(s) which act(s) as catcher of the antigen (a) and/or the receptor(s) which act(s) as detector of the antigen (b) is/are replaced by an immune complex each, which in case
- consists of at least one unlabelled antibody specifically binding the antigen and one labelled antibody specifically binding the at least one unlabelled antibody, which in case
- consists of at least one non-immobilised antibody specifically binding the antigen and one antibody immobilised at the test line specifically binding said at least one non-immobilised antibody.

44. The testing means according to any one of claims 39 to 42, wherein the receptor and/or the mixture of receptors bind(s) (a) conformation epitope(s).

45. The testing means according to any one of claims 38 to 42, wherein the heavy chain of the antibody binding a catalase epitope exhibits at least one of the following CDRs:

CDR1: SEQ ID NO.:9
CDR2: SEQ ID NO.:10
CDR3: SEQ ID NO.:11
and wherein the DNA sequence encoding the heavy chain of the antibody exhibits at least one of the following CDRs:
CDR1: SEQ ID NO.:12
CDR2: —SEQ ID NO.:13
CDR3: SEQ ID NO.:14
and wherein the light chain of the antibody binding a catalase epitope exhibits at least one of the following CDRs:
CDR1: SEQ ID NO.:15
CDR2: SEQ ID NO.:16
CDR3: SEQ ID NO.:17
and wherein the DNA sequence encoding the light chain of the antibody exhibits at least one of the following CDRs:
CDR1: SEQ ID NO.:18
CDR2: SEQ ID NO.:19
CDR3: SEQ ID NO.:20.

46. The testing means according to any one of claims 38 to 42, wherein the heavy chain of the antibody binding a catalase epitope exhibits at least one of the following CDRs:
CDR1: SEQ ID NO.:21
CDR2: SEQ ID NO.:22
CDR3: SEQ ID NO.:23
and wherein the DNA sequence encoding the heavy chain of the antibody exhibits at least one of the following CDRs:
CDR1: SEQ ID NO.:24
CDR2: SEQ ID NO.:25
CDR3: SEQ ID NO.:26
and wherein the light chain of the antibody binding a catalase epitope exhibits at least one of the following CDRs:
CDR1: SEQ ID NO.:27
CDR2: SEQ ID NO.:28
CDR3: SEQ ID NO.:29
and wherein the DNA sequence encoding the light chain of the antibody exhibits at least one of the following CDRs:
CDR1: SEQ ID NO.:30
CDR2: SEQ ID NO.:31
CDR3: SEQ ID NO.:32.

47. The testing means according to any one of the claims 38 to 42, wherein the heavy chain of the antibody binding an epitope of the β-urease exhibits at least one of the following CDRs:
CDR1: SEQ ID NO.:33
CDR2: SEQ ID NO.:34
CDR3: SEQ ID NO.:35
or
CDR1: SEQ ID NO.:36
CDR2: SEQ ID NO.:37
CDR3: SEQ ID NO.:38.

48. The testing means according to claim 47, wherein the DNA sequence of the antibody encoding the heavy chain exhibits at least one of the following CDRs:
CDR1: SEQ ID NO.:39
CDR2: SEQ ID NO.:40
CDR3: SEQ ID NO.:41
or
CDR1: SEQ ID NO.:42
CDR2: SEQ ID NO.:43
CDR3: SEQ ID NO.:44.

49. The testing means according to any one of claims 38 to 42, wherein the light chain of the antibody binding an epitope of the β-urease exhibits at least one of the following CDR:
CDR1: SEQ ID NO.:45
CDR2: SEQ ID NO.:46
CDR3: SEQ ID NO 47
or
CDR1: SEQ ID NO.:48
CDR2: SEQ ID NO.:49
CDR3: SEQ ID NO.:50.

50. The testing means according to claim 49, wherein the DNA sequence of the antibody encoding the light chain exhibits at least one of the following CDRs:
CDR1: SEQ ID NO.:51
CDR2: SEQ ID NO.:52
CDR3: SEQ ID NO.:53
or
CDR1: SEQ ID NO.:54
CDR2: SEQ ID NO.:55
CDR3: SEQ ID NO.:56.

51. The testing means according to any one of claims 38 to 42, wherein the antibodies in the variable regions of the light and heavy chains exhibit the DNA sequences SEQ ID NOS. 2 and 1, SEQ ID NOS. 3 and 2, SEQ ID NOS. 3 and 4, SEQ ID NOS. 6 and 5 and SEQ ID NOS. 8 and 7, respectively.

52. The testing means according to any one of claims 38 to 42, wherein the coding regions of the variable regions of the light and heavy chains exhibit the amino acid sequences of SEQ ID NOS. 84 and 83, SEQ ID NOS. 84 and 85, SEQ ID NOS. 86 and 85, SEQ ID NOS. 87 and 88, and SEQ ID NOS. 89 and 90, respectively.

53. The testing means according to claim 24, wherein the step of resuspending the stool sample in a sample buffer is carried out with the stool sample before the incubation with the antibodies, said stool sample being in the ratio of 1:3 to 1:25.

54. The testing means according to claim 24, wherein the same receptor is used for binding to the solid phase as is used for the detection of the epitope.

55. The testing means according to claim 24, wherein the receptor is a monoclonal mouse antibody.

56. The testing means according to claim 24, wherein the mammal is a human.

57. A kit containing at least one testing means according to any one of claims 24, 25–30, and 31–Δand 53–56.

58. The testing means according to claim 24, wherein the acid-resistant bacterium is *Helicobacter pylori* and wherein the antigen is a urease.

59. The testing means according to claim 24, wherein the acid-resistant bacterium is *Helicobacter pylori* and wherein the antigen is a metalloproteinase.

60. A method for detecting an infection of a mammal with an acid-resistant microorganism belonging to the genus *Helicobacter*, comprising:
(a) provision of an immunochromatographic rapid test with a sample application area for the application of a stool sample of the mammal with an antigen and application of the stool sample,
(b) incubation of the stool sample using (i) a first receptor under conditions permitting a complex formation of the antigen from the acid resistant microorganism with the receptor; or (ii) at least one of two different first receptors under conditions permitting a complex formation of the antigen from the acid-resistant microorganism with the at least one of two different first receptors and wherein the first receptor according to (i) or the at least one of two different first receptors according to (ii) specifically bind(s) to at least one epitope of an antigen which shows, at least with some mammals, a structure after passage through the intestine that corresponds to the native structure or the structure against which a mammal produces antibodies against after being infected or immunized with the acid-resistant microorganism or an extract or lysate thereof or a protein therefrom or a fragment thereof or a synthetic peptide, wherein said at least one epitope is an epitope of an antigen or antigens selected from the group consisting of a catalase, urease and metalloproteinase; and wherein at least one epitope of antigen or antigens specifically bind(s) to the heavy or light chain of the catalase or urease antibody having at least one of the CDRs: SEQ ID NOS:9, 10, 11, 21, 22, 23, 33–38, or SEQ ID NOS:15, 16, 17, 27, 28, 29, 45–50, respectively; and (c) provision of a second receptor immobilized at an analysis area, wherein the second receptor binds an antigen receptor complex according to (b), and transport and detection of the formation of at least one antigen receptor complex according to (b) by formation of the antigen-receptor complex at the second receptor in the analysis area.

* * * * *

SEQUENCE LISTING

<160> NUMBER OF SEQ ID NOS: 90

<210> SEQ ID NO 1
<211> LENGTH: 354
<212> TYPE: DNA
<213> ORGANISM: Mus musculus

<400> SEQUENCE: 1

```
gaggtgcagc tgctcgagca gcctggggct gaactggcaa aacctggggc tcagtgaag      60 atgtcctgca aggcttctgg ctacaccttt actaactact ggattcactg ggtgaaacag    120
aggcctggac agggtctgaa atggattgga tacattaatc ctgccactgg ttccacttct    180
tacaatcagg actttcagga cagggccact ttgaccgcag acaagtcctc caccacagcc    240
tacatgcagc tgaccagcct gacatctgag gactcttcag tctattactg tgcaagagag    300
gggtacgacg ggtttgactc ctggggccaa ggcaccactc tcacagtctc ctca          354
```

<210> SEQ ID NO 2
<211> LENGTH: 318
<212> TYPE: DNA
<213> ORGANISM: Mus musculus

<400> SEQUENCE: 2

```
gagctcgtgc tcacccagtc tccagcaatc atgtctgcat ctccagggga gaaggtcacc      60
atgacctgca gtgccagctc aagtgtaaat tacatgtact ggtaccagca gaagtcaggc    120
acctccccca aaagatggat ttatgacaca tccaaattgg cttctggagt ccctgctcgc    180
ttcagtggca gtgggtctgg gacctcttac tctctcacac tcagcagcat ggaggctgaa    240
```

```
gatgccgcca cttattactg ccagcagtgg agtagtaatc cgtacacgtt cggagggggg      300
accaagctgg agataaaa                                                     318
```

```
<210> SEQ ID NO 3
<211> LENGTH: 360
<212> TYPE: DNA
<213> ORGANISM: Mus musculus

<400> SEQUENCE: 3
gaggttcagc tgcagcagtc tggggcagag cttgtgaagc ctggggcctc agtcaagttg       60
tcctgcacat cttctggctt caacattaaa gacacctatg tgcactggat gaaacagagg      120
cctgaacagg gcctggagtg gattggaaag attgatcctg cgaatggtaa aactaaatat      180
gacccgatat tccaggccaa ggccactatg acagcagacg catcctccaa tacagcctac      240
ctgcaactca gcagcctgac ttctgaggac actgccgtct attactgtgc ctctcccatt      300
tattacgcta gttcctggtt tgcttactgg ggccaaggga ctctggtcac tgtctctgca      360
```

```
<210> SEQ ID NO 4
<211> LENGTH: 318
<212> TYPE: DNA
<213> ORGANISM: Mus musculus

<400> SEQUENCE: 4
gacattgtga tgacccagtc tcacaaattc atgtccacat cagtaggaga cagggtcagc       60
atcacctgca aggccagtca ggatgtgggt acttctgttg cctggtatca acagaaacct      120
gggcactctc ctaaattact gatttactgg acatccaccc ggcacacagg agtccctgat      180
cgcttcacag gcagtggatc tgggacagat ttcattctca ccattagcaa tgtgcagtct      240
gaagacttgg cagattattt ctgtcagcaa tatagcagct cccacgtt cggaggggg        300 gccaaggtgg aaataaaa                                                    318
```

```
<210> SEQ ID NO 5
<211> LENGTH: 321
<212> TYPE: DNA
<213> ORGANISM: Mus musculus

<400> SEQUENCE: 5
gacatcttgc tgactcagtc tccagccatc ctgtctgtga gtccaggaga aagagtcagt       60
ttctcctgca gggccagtca gagcattggc acaagaatac actggtatca acaagaaca      120 aatggttctc caaggcttct cataaagtat ggttctgagt ctatctctgg gatcccttcc      180
aggtttagtg gcagtggatc agggacagat tttagtctta gcatcaacag tgtcgagtct      240
gaagacattg cagattatta ctgtcaacaa agtaatacct ggccgctcac gttcggtgct      300
gggaccaagc tggagctgaa a                                                321
```

```
<210> SEQ ID NO 6
<211> LENGTH: 369
<212> TYPE: DNA
<213> ORGANISM: Mus musculus

<400> SEQUENCE: 6
gaggtgcagc tgctcgagca gtctggagct gagctggtga agcctggggc ctcagtgaag       60
atttcctgca aggcttctgg ctacgcattc agtacctcct ggatgaactg ggtgaaacag      120
aggcctggaa aggtcttga gtggattgga cggatttatc ctgagatgg agatactaac      180
```

```
tacaatggga agttcaaggg caaggccaca ctgactgcag acaaatcctc cagcacagcc    240
tacatgcaac tcaacagcct gacatctgag gactctgcgg tctacttctg tgtaagagag    300
gatgcctatt atagtaaccc ctatagtttg gactactggg gtcaaggaac ctcagtcacc    360
gtctcctca                                                              369

<210> SEQ ID NO 7
<211> LENGTH: 321
<212> TYPE: DNA
<213> ORGANISM: Mus musculus

<400> SEQUENCE: 7
gagctccaga tgacccagtc tccatccagt ctgtctgcat cccttggaga cacaattacc     60
atcacttgcc atgccagtca gaacattaat gtttggttaa gctggtatca gcagaaacca    120
ggagatatcc ctaaactatt gatctataag gcttccaact tgcacacagg cgtcccatca    180
aggtttagtg gcagtggatc tggaacaggt ttcacattag tcatcagcag cctgcagcct    240
gaagacattg ccacttacta ctgtcaacag ggtcgaagtt atcctctcac gttcggtgct    300
gggaccaagc tggagctgaa a                                              321

<210> SEQ ID NO 8
<211> LENGTH: 354
<212> TYPE: DNA
<213> ORGANISM: Mus musculus

<400> SEQUENCE: 8
gaggtgcagc tgctcgagga gtctggggga ggcttagtga agcctggagg gtccctgcaa     60
ctctcctgtt cagcctctgg attcactttc agtagccatt tcatgtcttg ggttcgccaa    120
actccagaga gaggctggag gtgggtcgca tccattagta gtggtggtga cagtttctat    180
ccagacagtc tgaagggccg attcgccatc tccagagata tgccaggaa catcctgttc    240 ctgcaaatga gcagtctgag gtctgaggac tcggccatgt atttctgtac aagagactac    300
tcttggtatg ctttggacta ctggggtcaa ggaacctcag tcaccgtctc ctca          354

<210> SEQ ID NO 9
<211> LENGTH: 5
<212> TYPE: PRT
<213> ORGANISM: Artificial
<220> FEATURE:
<223> OTHER INFORMATION: Description of Artificial Sequence:  CDR

<400> SEQUENCE: 9

Asn Tyr Trp Ile His
1               5

<210> SEQ ID NO 10
<211> LENGTH: 17
<212> TYPE: PRT
<213> ORGANISM: Artificial
<220> FEATURE:
<223> OTHER INFORMATION: Description of Artificial Sequence: CDR

<400> SEQUENCE: 10

Tyr Ile Asn Pro Ala Thr Gly Ser Thr Ser Tyr Asn Gln Asp Phe Gln
1               5                   10                  15

Asp

<210> SEQ ID NO 11
<211> LENGTH: 8
```

```
<212> TYPE: PRT
<213> ORGANISM: Artificial
<220> FEATURE:
<223> OTHER INFORMATION: Description of Artificial Sequence: CDR

<400> SEQUENCE: 11

Glu Gly Tyr Asp Gly Phe Asp Ser
1               5

<210> SEQ ID NO 12
<211> LENGTH: 15
<212> TYPE: DNA
<213> ORGANISM: Artificial
<220> FEATURE:
<223> OTHER INFORMATION: Description of Artificial Sequence: CDR

<400> SEQUENCE: 12
aactactgga ttcac                                                    15

<210> SEQ ID NO 13
<211> LENGTH: 51
<212> TYPE: DNA
<213> ORGANISM: Artificial
<220> FEATURE:
<223> OTHER INFORMATION: Description of Artificial Sequence: CDR

<400> SEQUENCE: 13
tacattaatc ctgccactgg ttccacttct tacaatcagg actttcagga c            51

<210> SEQ ID NO 14
<211> LENGTH: 24
<212> TYPE: DNA
<213> ORGANISM: Artificial
<220> FEATURE:
<223> OTHER INFORMATION: Description of Artificial Sequence: CDR

<400> SEQUENCE: 14 gagggtacg acgggtttga ctcc                                           24

<210> SEQ ID NO 15
<211> LENGTH: 10
<212> TYPE: PRT
<213> ORGANISM: Artificial
<220> FEATURE:
<223> OTHER INFORMATION: Description of Artificial Sequence: CDR

<400> SEQUENCE: 15

Ser Ala Ser Ser Ser Val Asn Tyr Met Tyr
1               5                   10

<210> SEQ ID NO 16
<211> LENGTH: 7
<212> TYPE: PRT
<213> ORGANISM: Artificial
<220> FEATURE:
<223> OTHER INFORMATION: Description of Artificial Sequence: CDR

<400> SEQUENCE: 16

Asp Thr Ser Lys Leu Ala Ser
1               5

<210> SEQ ID NO 17
<211> LENGTH: 9
<212> TYPE: PRT
<213> ORGANISM: Artificial
<220> FEATURE:
<223> OTHER INFORMATION: Description of Artificial Sequence: CDR
```

```
<400> SEQUENCE: 17

Gln Gln Trp Ser Ser Asn Pro Tyr Thr
1               5

<210> SEQ ID NO 18
<211> LENGTH: 30
<212> TYPE: DNA
<213> ORGANISM: Artificial
<220> FEATURE:
<223> OTHER INFORMATION: Description of Artificial Sequence:  CDR

<400> SEQUENCE: 18
agtgccagct caagtgtaaa ttacatgtac                                       30

<210> SEQ ID NO 19
<211> LENGTH: 21
<212> TYPE: DNA
<213> ORGANISM: Artificial
<220> FEATURE:
<223> OTHER INFORMATION: Description of Artificial Sequence:  CDR

<400> SEQUENCE: 19
gacacatcca aattggcttc t                                                21

<210> SEQ ID NO 20
<211> LENGTH: 27
<212> TYPE: DNA
<213> ORGANISM: Artificial
<220> FEATURE:
<223> OTHER INFORMATION: Description of Artificial Sequence:  CDR

<400> SEQUENCE: 20
cagcagtgga gtagtaatcc gtacacg                                          27

<210> SEQ ID NO 21
<211> LENGTH: 5
<212> TYPE: PRT
<213> ORGANISM: Artificial
<220> FEATURE:
<223> OTHER INFORMATION: Description of Artificial Sequence:  CDR

<400> SEQUENCE: 21

Asp Thr Tyr Val His
1               5

<210> SEQ ID NO 22
<211> LENGTH: 17
<212> TYPE: PRT
<213> ORGANISM: Artificial
<220> FEATURE:
<223> OTHER INFORMATION: Description of Artificial Sequence:  CDR

<400> SEQUENCE: 22

Lys Ile Asp Pro Ala Asn Gly Lys Thr Lys Tyr Asp Pro Ile Phe Gln
1               5                   10                  15

Ala

<210> SEQ ID NO 23
<211> LENGTH: 11
<212> TYPE: PRT
<213> ORGANISM: Artificial
<220> FEATURE:
<223> OTHER INFORMATION: Description of Artificial Sequence:  CDR

<400> SEQUENCE: 23
```

Pro Ile Tyr Tyr Ala Ser Ser Trp Phe Ala Tyr
1               5                   10

<210> SEQ ID NO 24
<211> LENGTH: 15
<212> TYPE: DNA
<213> ORGANISM: Artificial
<220> FEATURE:
<223> OTHER INFORMATION: Description of Artificial Sequence: CDR

<400> SEQUENCE: 24
gacacctatg tgcac                                                        15

<210> SEQ ID NO 25
<211> LENGTH: 51
<212> TYPE: DNA
<213> ORGANISM: Artificial
<220> FEATURE:
<223> OTHER INFORMATION: Description of Artificial Sequence: CDR

<400> SEQUENCE: 25
aagattgatc ctgcgaatgg taaaactaaa tatgacccga tattccaggc c                 51

<210> SEQ ID NO 26
<211> LENGTH: 33
<212> TYPE: DNA
<213> ORGANISM: Artificial
<220> FEATURE:
<223> OTHER INFORMATION: Description of Artificial Sequence: CDR

<400> SEQUENCE: 26
cccatttatt acgctagttc ctggtttgct tac                                    33

<210> SEQ ID NO 27
<211> LENGTH: 11
<212> TYPE: PRT
<213> ORGANISM: Artificial
<220> FEATURE:
<223> OTHER INFORMATION: Description of Artificial Sequence: CDR

<400> SEQUENCE: 27

Lys Ala Ser Gln Asp Val Gly Thr Ser Val Ala
1               5                   10

<210> SEQ ID NO 28
<211> LENGTH: 7
<212> TYPE: PRT
<213> ORGANISM: Artificial
<220> FEATURE:
<223> OTHER INFORMATION: Description of Artificial Sequence: CDR

<400> SEQUENCE: 28

Trp Thr Ser Thr Arg His Thr
1               5

<210> SEQ ID NO 29
<211> LENGTH: 8
<212> TYPE: PRT
<213> ORGANISM: Artificial
<220> FEATURE:
<223> OTHER INFORMATION: Description of Artificial Sequence: CDR

<400> SEQUENCE: 29

Gln Gln Tyr Ser Ser Ser Pro Thr
1               5

```
<210> SEQ ID NO 30
<211> LENGTH: 33
<212> TYPE: DNA
<213> ORGANISM: Artificial
<220> FEATURE:
<223> OTHER INFORMATION: Description of Artificial Sequence:  CDR

<400> SEQUENCE: 30
aaggccagtc aggatgtggg tacttctgtt gcc                           33

<210> SEQ ID NO 31
<211> LENGTH: 21
<212> TYPE: DNA
<213> ORGANISM: Artificial
<220> FEATURE:
<223> OTHER INFORMATION: Description of Artificial Sequence:  CDR

<400> SEQUENCE: 31
tggacatcca cccggcacac t                                        21

<210> SEQ ID NO 32
<211> LENGTH: 24
<212> TYPE: DNA
<213> ORGANISM: Artificial
<220> FEATURE:
<223> OTHER INFORMATION: Description of Artificial Sequence:  CDR

<400> SEQUENCE: 32
cagcaatata gcagctctcc cacg                                     24

<210> SEQ ID NO 33
<211> LENGTH: 10
<212> TYPE: PRT
<213> ORGANISM: Artificial
<220> FEATURE:
<223> OTHER INFORMATION: Description of Artificial Sequence:  CDR

<400> SEQUENCE: 33

Gly Phe Thr Phe Ser Ser His Phe Met Ser
1               5                   10

<210> SEQ ID NO 34
<211> LENGTH: 16
<212> TYPE: PRT
<213> ORGANISM: Artificial
<220> FEATURE:
<223> OTHER INFORMATION: Description of Artificial Sequence:  CDR

<400> SEQUENCE: 34

Ser Ile Ser Ser Gly Gly Asp Ser Phe Tyr Pro Asp Ser Leu Lys Gly
1               5                   10                  15

<210> SEQ ID NO 35
<211> LENGTH: 9
<212> TYPE: PRT
<213> ORGANISM: Artificial
<220> FEATURE:
<223> OTHER INFORMATION: Description of Artificial Sequence:  CDR

<400> SEQUENCE: 35

Asp Tyr Ser Trp Tyr Ala Leu Asp Tyr
1               5

<210> SEQ ID NO 36
<211> LENGTH: 10
<212> TYPE: PRT
```

```
<213> ORGANISM: Artificial
<220> FEATURE:
<223> OTHER INFORMATION: Description of Artificial Sequence:  CDR

<400> SEQUENCE: 36

Gly Tyr Ala Phe Ser Thr Ser Trp Met Asn
1               5                   10

<210> SEQ ID NO 37
<211> LENGTH: 17
<212> TYPE: PRT
<213> ORGANISM: Artificial
<220> FEATURE:
<223> OTHER INFORMATION: Description of Artificial Sequence:  CDR

<400> SEQUENCE: 37

Arg Ile Tyr Pro Gly Asp Gly Asp Thr Asn Tyr Asn Gly Lys Phe Lys
1               5                   10                  15

Gly

<210> SEQ ID NO 38
<211> LENGTH: 13
<212> TYPE: PRT
<213> ORGANISM: Artificial
<220> FEATURE:
<223> OTHER INFORMATION: Description of Artificial Sequence:  CDR

<400> SEQUENCE: 38

Glu Asp Ala Tyr Tyr Ser Asn Pro Tyr Ser Leu Asp Tyr
1               5                   10

<210> SEQ ID NO 39
<211> LENGTH: 30
<212> TYPE: DNA
<213> ORGANISM: Artificial
<220> FEATURE:
<223> OTHER INFORMATION: Description of Artificial Sequence:  CDR

<400> SEQUENCE: 39
ggctacgcat tcagtacctc ctggatgaac                                      30

<210> SEQ ID NO 40
<211> LENGTH: 51
<212> TYPE: DNA
<213> ORGANISM: Artificial
<220> FEATURE:
<223> OTHER INFORMATION: Description of Artificial Sequence:  CDR

<400> SEQUENCE: 40
cggatttatc ctggagatgg agatactaac tacaatggga agttcaaggg c              51

<210> SEQ ID NO 41
<211> LENGTH: 39
<212> TYPE: DNA
<213> ORGANISM: Artificial
<220> FEATURE:
<223> OTHER INFORMATION: Description of Artificial Sequence:  CDR

<400> SEQUENCE: 41
gaggatgcct attatagtaa cccctatagt ttggactac                            39

<210> SEQ ID NO 42
<211> LENGTH: 30
<212> TYPE: DNA
<213> ORGANISM: Artificial
<220> FEATURE:
```

<223> OTHER INFORMATION: Description of Artificial Sequence: CDR

<400> SEQUENCE: 42
ggattcactt tcagtagcca tttcatgtct                              30

<210> SEQ ID NO 43
<211> LENGTH: 48
<212> TYPE: DNA
<213> ORGANISM: Artificial
<220> FEATURE:
<223> OTHER INFORMATION: Description of Artificial Sequence: CDR

<400> SEQUENCE: 43
tccattagta gtggtggtga cagtttctat ccagacagtc tgaagggc          48

<210> SEQ ID NO 44
<211> LENGTH: 27
<212> TYPE: DNA
<213> ORGANISM: Artificial
<220> FEATURE:
<223> OTHER INFORMATION: Description of Artificial Sequence: CDR

<400> SEQUENCE: 44
gactactctt ggtatgcttt ggactac                                 27

<210> SEQ ID NO 45
<211> LENGTH: 11
<212> TYPE: PRT
<213> ORGANISM: Artificial
<220> FEATURE:
<223> OTHER INFORMATION: Description of Artificial Sequence: CDR

<400> SEQUENCE: 45

Arg Ala Ser Gln Ser Ile Gly Thr Arg Ile His
1               5                   10

<210> SEQ ID NO 46
<211> LENGTH: 7
<212> TYPE: PRT
<213> ORGANISM: Artificial
<220> FEATURE:
<223> OTHER INFORMATION: Description of Artificial Sequence: CDR

<400> SEQUENCE: 46

Tyr Gly Ser Glu Ser Ile Ser
1               5

<210> SEQ ID NO 47
<211> LENGTH: 9
<212> TYPE: PRT
<213> ORGANISM: Artificial
<220> FEATURE:
<223> OTHER INFORMATION: Description of Artificial Sequence: CDR

<400> SEQUENCE: 47

Gln Gln Ser Asn Thr Trp Pro Leu Thr
1               5

<210> SEQ ID NO 48
<211> LENGTH: 11
<212> TYPE: PRT
<213> ORGANISM: Artificial
<220> FEATURE:
<223> OTHER INFORMATION: Description of Artificial Sequence: CDR

<400> SEQUENCE: 48

```
His Ala Ser Gln Asn Ile Asn Val Trp Leu Ser
1               5                   10
```

<210> SEQ ID NO 49
<211> LENGTH: 7
<212> TYPE: PRT
<213> ORGANISM: Artificial
<220> FEATURE:
<223> OTHER INFORMATION: Description of Artificial Sequence:   CDR

<400> SEQUENCE: 49

```
Lys Ala Ser Asn Leu His Thr
1               5
```

<210> SEQ ID NO 50
<211> LENGTH: 9
<212> TYPE: PRT
<213> ORGANISM: Artificial
<220> FEATURE:
<223> OTHER INFORMATION: Description of Artificial Sequence:   CDR

<400> SEQUENCE: 50

```
Gln Gln Gly Arg Ser Tyr Pro Leu Thr
1               5
```

<210> SEQ ID NO 51
<211> LENGTH: 33
<212> TYPE: DNA
<213> ORGANISM: Artificial
<220> FEATURE:
<223> OTHER INFORMATION: Description of Artificial Sequence:   CDR

<400> SEQUENCE: 51
agggccagtc agagcattgg cacaagaata cac                           33

<210> SEQ ID NO 52
<211> LENGTH: 21
<212> TYPE: DNA
<213> ORGANISM: Artificial
<220> FEATURE:
<223> OTHER INFORMATION: Description of Artificial Sequence:   CDR

<400> SEQUENCE: 52
tatggttctg agtctatctc t                                        21

<210> SEQ ID NO 53
<211> LENGTH: 27
<212> TYPE: DNA
<213> ORGANISM: Artificial
<220> FEATURE:
<223> OTHER INFORMATION: Description of Artificial Sequence:   CDR

<400> SEQUENCE: 53
caacaaagta atacctggcc gctcacg                                  27

<210> SEQ ID NO 54
<211> LENGTH: 33
<212> TYPE: DNA
<213> ORGANISM: Artificial
<220> FEATURE:
<223> OTHER INFORMATION: Description of Artificial Sequence:   CDR

<400> SEQUENCE: 54
catgccagtc agaacattaa tgtttggtta agc                           33

<210> SEQ ID NO 55

```
<211> LENGTH: 21
<212> TYPE: DNA
<213> ORGANISM: Artificial
<220> FEATURE:
<223> OTHER INFORMATION: Description of Artificial Sequence:  CDR

<400> SEQUENCE: 55
aaggcttcca acttgcacac a                                          21

<210> SEQ ID NO 56
<211> LENGTH: 27
<212> TYPE: DNA
<213> ORGANISM: Artificial
<220> FEATURE:
<223> OTHER INFORMATION: Description of Artificial Sequence:  CDR

<400> SEQUENCE: 56
caacagggtc gaagttatcc tctcacg                                    27

<210> SEQ ID NO 57
<211> LENGTH: 17
<212> TYPE: PRT
<213> ORGANISM: Artificial
<220> FEATURE:
<223> OTHER INFORMATION: LysC peptide

<400> SEQUENCE: 57

Glu Arg Leu His Asp Thr Ile Gly Glu Ser Leu Ala His Val Thr His
 1               5                  10                  15

Lys

<210> SEQ ID NO 58
<211> LENGTH: 28
<212> TYPE: DNA
<213> ORGANISM: Artificial
<220> FEATURE:
<223> OTHER INFORMATION: PCR primer - MVH1

<400> SEQUENCE: 58
gcaggtgcag ctcgaggagt caggacct                                   28

<210> SEQ ID NO 59
<211> LENGTH: 27
<212> TYPE: DNA
<213> ORGANISM: Artificial
<220> FEATURE:
<223> OTHER INFORMATION: PCR Primer - MVH2

<400> SEQUENCE: 59
gaggtccagc tcgagcagtc tggacct                                    27

<210> SEQ ID NO 60
<211> LENGTH: 27
<212> TYPE: DNA
<213> ORGANISM: Artificial
<220> FEATURE:
<223> OTHER INFORMATION: PCR Primer - MVH3

<400> SEQUENCE: 60
caggtccaac tcgagcagcc tggggct                                    27

<210> SEQ ID NO 61
<211> LENGTH: 27
<212> TYPE: DNA
<213> ORGANISM: Artificial
<220> FEATURE:
```

```
<223> OTHER INFORMATION: PCR Primer - MVH4

<400> SEQUENCE: 61
gaggttcagc tcgagcagtc tggggca                                27

<210> SEQ ID NO 62
<211> LENGTH: 28
<212> TYPE: DNA
<213> ORGANISM: Artificial
<220> FEATURE:
<223> OTHER INFORMATION: PCR Primer - MVH5

<400> SEQUENCE: 62
gaaggtgaag ctcgaggagt ctggagga                               28

<210> SEQ ID NO 63
<211> LENGTH: 27
<212> TYPE: DNA
<213> ORGANISM: Artificial
<220> FEATURE:
<223> OTHER INFORMATION: PCR Primer - MVH6

<400> SEQUENCE: 63
gaggtgaagc ttctcgagtc tggaggt                                27

<210> SEQ ID NO 64
<211> LENGTH: 27
<212> TYPE: DNA
<213> ORGANISM: Artificial
<220> FEATURE:
<223> OTHER INFORMATION: PCR Primer - MVH7

<400> SEQUENCE: 64
gaagtgaagc tcgaggagtc tggggga                                27

<210> SEQ ID NO 65
<211> LENGTH: 27
<212> TYPE: DNA
<213> ORGANISM: Artificial
<220> FEATURE:
<223> OTHER INFORMATION: PCR Primer - MVH8

<400> SEQUENCE: 65
gaggttcagc tcgagcagtc tggagct                                27

<210> SEQ ID NO 66
<211> LENGTH: 38
<212> TYPE: DNA
<213> ORGANISM: Artificial
<220> FEATURE:
<223> OTHER INFORMATION: PCR Primer - MULK1

<400> SEQUENCE: 66
ggggagctcc accatggaga cagacacact cctgctat                    38

<210> SEQ ID NO 67
<211> LENGTH: 39
<212> TYPE: DNA
<213> ORGANISM: Artificial
<220> FEATURE:
<223> OTHER INFORMATION: PCR Primer - MULK2

<400> SEQUENCE: 67
ggggagctcc accatggatt tcaagtgca gattttcag                    39
```

<210> SEQ ID NO 68
<211> LENGTH: 40
<212> TYPE: DNA
<213> ORGANISM: Artificial
<220> FEATURE:
<223> OTHER INFORMATION: PCR Primer - MULK3

<400> SEQUENCE: 68
ggggagctcc accatggagw cacakwctca ggtctttrta        40

<210> SEQ ID NO 69
<211> LENGTH: 36
<212> TYPE: DNA
<213> ORGANISM: Artificial
<220> FEATURE:
<223> OTHER INFORMATION: PCR Primer - MULK4

<400> SEQUENCE: 69
ggggagctcc accatgkccc cwrctcagyt yctkgt        36

<210> SEQ ID NO 70
<211> LENGTH: 30
<212> TYPE: DNA
<213> ORGANISM: Artificial
<220> FEATURE:
<223> OTHER INFORMATION: PCR Primer - MlgG1

<400> SEQUENCE: 70
tatgcaacta gtacaaccac aatccctggg        30

<210> SEQ ID NO 71
<211> LENGTH: 36
<212> TYPE: DNA
<213> ORGANISM: Artificial
<220> FEATURE:
<223> OTHER INFORMATION: PCR Primer - MlgG2

<400> SEQUENCE: 71
gagagagggg ttctgactag tgggcactct gggctc        36

<210> SEQ ID NO 72
<211> LENGTH: 32
<212> TYPE: DNA
<213> ORGANISM: Artificial
<220> FEATURE:
<223> OTHER INFORMATION: PCR Primer - MUVK1

<400> SEQUENCE: 72
ccagttccga gctcgttgtg actcaggatt ct        32

<210> SEQ ID NO 73
<211> LENGTH: 32
<212> TYPE: DNA
<213> ORGANISM: Artificial
<220> FEATURE:
<223> OTHER INFORMATION: PCR Primer - MUVK2

<400> SEQUENCE: 73
ccagttccga gctcgtgttg acgcagccgc cc        32

<210> SEQ ID NO 74
<211> LENGTH: 32
<212> TYPE: DNA
<213> ORGANISM: Artificial
<220> FEATURE:
<223> OTHER INFORMATION: PCR Primer - MUVK3

```
<400> SEQUENCE: 74
ccagttccga gctcgtgctc acccagtctc ca                        32

<210> SEQ ID NO 75
<211> LENGTH: 32
<212> TYPE: DNA
<213> ORGANISM: Artificial
<220> FEATURE:
<223> OTHER INFORMATION: PCR Primer - MUVK4

<400> SEQUENCE: 75
ccagttccga gctccagatg acccagtctc ca                        32

<210> SEQ ID NO 76
<211> LENGTH: 32
<212> TYPE: DNA
<213> ORGANISM: Artificial
<220> FEATURE:
<223> OTHER INFORMATION: PCR Primer - MUVK5

<400> SEQUENCE: 76
ccagatgtga gctcgtgatg acccagactc ca                        32

<210> SEQ ID NO 77
<211> LENGTH: 32
<212> TYPE: DNA
<213> ORGANISM: Artificial
<220> FEATURE:
<223> OTHER INFORMATION: PCR Primer - MUVK6

<400> SEQUENCE: 77
ccagatgtga gctcgtcatg acccagtctc ca                        32

<210> SEQ ID NO 78
<211> LENGTH: 32
<212> TYPE: DNA
<213> ORGANISM: Artificial
<220> FEATURE:
<223> OTHER INFORMATION: PCR Primer - MUVK7

<400> SEQUENCE: 78
ccagttccga gctcgtgatg acacagtctc ca                        32

<210> SEQ ID NO 79
<211> LENGTH: 39
<212> TYPE: DNA
<213> ORGANISM: Artificial
<220> FEATURE:
<223> OTHER INFORMATION: PCR Primer - MULH1

<400> SEQUENCE: 79
gggctcgagc accatggrat gsagctgkgt matsctctt                 39

<210> SEQ ID NO 80
<211> LENGTH: 39
<212> TYPE: DNA
<213> ORGANISM: Artificial
<220> FEATURE:
<223> OTHER INFORMATION: PCR Primer - MULH2

<400> SEQUENCE: 80
gggctcgagc accatgract cggggytgag ctkggtttt                 39

<210> SEQ ID NO 81
<211> LENGTH: 38
```

```
<212> TYPE: DNA
<213> ORGANISM: Artificial
<220> FEATURE:
<223> OTHER INFORMATION: PCR Primer - MULH3

<400> SEQUENCE: 81
gggctcgagc accatggctg tcttggggct gctcttct                              38

<210> SEQ ID NO 82
<211> LENGTH: 34
<212> TYPE: DNA
<213> ORGANISM: Artificial
<220> FEATURE:
<223> OTHER INFORMATION: PCR Primer - 3' MUCK

<400> SEQUENCE: 82
gcgccgtcta gaattaacac tcattcctgt tgaa                                  34

<210> SEQ ID NO 83
<211> LENGTH: 118
<212> TYPE: PRT
<213> ORGANISM: Mus musculus

<400> SEQUENCE: 83
```

Glu Val Gln Leu Leu Glu Gln Pro Gly Ala Glu Leu Ala Lys Pro Gly
1               5                   10                  15

Ala Ser Val Lys Met Ser Cys Lys Ala Ser Gly Tyr Thr Phe Thr Asn
                20                  25                  30

Tyr Trp Ile His Trp Val Lys Gln Arg Pro Gly Gln Gly Leu Lys Trp
            35                  40                  45

Ile Gly Tyr Ile Asn Pro Ala Thr Gly Ser Thr Ser Tyr Asn Gln Asp
    50                  55                  60

Phe Gln Asp Arg Ala Thr Leu Thr Ala Asp Lys Ser Ser Thr Thr Ala
65                  70                  75                  80

Tyr Met Gln Leu Thr Ser Leu Thr Ser Glu Asp Ser Ser Val Tyr Tyr
                85                  90                  95

Cys Ala Arg Glu Gly Tyr Asp Gly Phe Asp Ser Trp Gly Gln Gly Thr
            100                 105                 110

Thr Leu Thr Val Ser Ser
        115

```
<210> SEQ ID NO 84
<211> LENGTH: 106
<212> TYPE: PRT
<213> ORGANISM: Mus musculus

<400> SEQUENCE: 84
```

Glu Leu Val Leu Thr Gln Ser Pro Ala Ile Met Ser Ala Ser Pro Gly
1               5                   10                  15

Glu Lys Val Thr Met Thr Cys Ser Ala Ser Ser Val Asn Tyr Met
                20                  25                  30

Tyr Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Leu Ser Met Glu Ala Glu
65                  70                  75                  80

Asp Ala Ala Thr Tyr Tyr Cys Gln Gln Trp Ser Ser Asn Pro Tyr Thr
                85                  90                  95

```
Phe Gly Gly Gly Thr Lys Leu Glu Ile Lys
            100                 105
```

<210> SEQ ID NO 85
<211> LENGTH: 120
<212> TYPE: PRT
<213> ORGANISM: Mus musculus

<400> SEQUENCE: 85

```
Glu Val Gln Leu Gln Gln Ser Gly Ala Glu Leu Val Lys Pro Gly Ala
1               5                   10                  15

Ser Val Lys Leu Ser Cys Thr Ser Ser Gly Phe Asn Ile Lys Asp Thr
            20                  25                  30

Tyr Val His Trp Met Lys Gln Arg Pro Glu Gln Gly Leu Glu Trp Ile
        35                  40                  45

Gly Lys Ile Asp Pro Ala Asn Gly Lys Thr Lys Tyr Asp Pro Ile Phe
    50                  55                  60

Gln Ala Lys Ala Thr Met Thr Ala Asp Ala Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Leu Pro Ile Tyr Tyr Ala Ser Ser Trp Phe Ala Tyr Trp Gly Gln
            100                 105                 110

Gly Thr Leu Val Thr Val Ser Ala
        115                 120
```

<210> SEQ ID NO 86
<211> LENGTH: 106
<212> TYPE: PRT
<213> ORGANISM: Mus musculus

<400> SEQUENCE: 86

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ser
            20                  25                  30

Val Ala Trp Tyr Gln Gln Lys Pro Gly His Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Phe Ile Leu Thr Ile Ser Asn Val Gln Ser
65                  70                  75                  80

Glu Asp Leu Ala Asp Tyr Phe Cys Gln Gln Tyr Ser Ser Ser Pro Thr
                85                  90                  95

Phe Gly Gly Gly Ala Lys Val Glu Ile Lys
            100                 105
```

<210> SEQ ID NO 87
<211> LENGTH: 107
<212> TYPE: PRT
<213> ORGANISM: Mus musculus

<400> SEQUENCE: 87

```
Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Arg
            20                  25                  30

Ile His Trp Tyr Gln Gln Arg Thr Asn Gly Ser Pro Arg Leu Leu Ile
```

```
                35                  40                  45
Lys Tyr Gly Ser Glu Ser Ile Ser Gly Ile Pro Ser Arg Phe Ser Gly
         50                  55                  60
Ser Gly Ser Gly Thr Asp Phe Ser Leu Ser Ile Asn Ser Val Glu Ser
 65                  70                  75                  80
Glu Asp Ile Ala Asp Tyr Tyr Cys Gln Gln Ser Asn Thr Trp Pro Leu
                 85                  90                  95
Thr Phe Gly Ala Gly Thr Lys Leu Glu Leu Lys
                100                 105
```

<210> SEQ ID NO 88
<211> LENGTH: 123
<212> TYPE: PRT
<213> ORGANISM: Mus musculus

<400> SEQUENCE: 88

```
Glu Val Gln Leu Leu Glu Gln Ser Gly Ala Glu Leu Val Lys Pro Gly
 1               5                  10                  15
Ala Ser Val Lys Ile Ser Cys Lys Ala Ser Gly Tyr Ala Phe Ser Thr
                20                  25                  30
Ser Trp Met Asn Trp Val Lys Gln Arg Pro Gly Lys Gly Leu Glu Trp
                35                  40                  45
Ile Gly Arg Ile Tyr Pro Gly Asp Gly Asp Thr Asn Tyr Asn Gly Lys
         50                  55                  60
Phe Lys Gly Lys Ala Thr Leu Thr Ala Asp Lys Ser Ser Ser Thr Ala
 65                  70                  75                  80
Tyr Met Gln Leu Asn Ser Leu Thr Ser Glu Asp Ser Ala Val Tyr Phe
                 85                  90                  95
Cys Val Arg Glu Asp Ala Tyr Tyr Ser Asn Pro Tyr Ser Leu Asp Tyr
                100                 105                 110
Trp Gly Gln Gly Thr Ser Val Thr Val Ser Ser
            115                 120
```

<210> SEQ ID NO 89
<211> LENGTH: 107
<212> TYPE: PRT
<213> ORGANISM: Mus musculus

<400> SEQUENCE: 89

```
Glu Leu Gln Met Thr Gln Ser Pro Ser Ser Leu Ser Ala Ser Leu Gly
 1               5                  10                  15
Asp Thr Ile Thr Ile Thr Cys His Ala Ser Gln Asn Ile Asn Val Trp
                20                  25                  30
Leu Ser Trp Tyr Gln Gln Lys Pro Gly Asp Ile Pro Lys Leu Leu Ile
                35                  40                  45
Tyr Lys Ala Ser Asn Leu His Thr Gly Val Pro Ser Arg Phe Ser Gly
         50                  55                  60
Ser Gly Ser Gly Thr Gly Phe Thr Leu Val Ile Ser Ser Leu Gln Pro
 65                  70                  75                  80
Glu Asp Ile Ala Thr Tyr Tyr Cys Gln Gln Gly Arg Ser Tyr Pro Leu
                 85                  90                  95
Thr Phe Gly Ala Gly Thr Lys Leu Glu Leu Lys
                100                 105
```

<210> SEQ ID NO 90
<211> LENGTH: 118
<212> TYPE: PRT

-continued

```
<213> ORGANISM: Mus musculus

<400> SEQUENCE: 90

Glu Val Gln Leu Leu Glu Glu Ser Gly Gly Gly Leu Val Lys Pro Gly
1               5                   10                  15

Gly Ser Leu Gln Leu Ser Cys Ser Ala Ser Gly Phe Thr Phe Ser Ser
            20                  25                  30

His Phe Met Ser Trp Val Arg Gln Thr Pro Glu Lys Arg Leu Glu Trp
        35                  40                  45

Val Ala Ser Ile Ser Ser Gly Gly Asp Ser Phe Tyr Pro Asp Ser Leu
    50                  55                  60

Lys Gly Arg Phe Ala Ile Ser Arg Asp Asn Ala Arg Asn Ile Leu Phe
65                  70                  75                  80

Leu Gln Met Ser Ser Leu Arg Ser Glu Asp Ser Ala Met Tyr Phe Cys
                85                  90                  95

Thr Arg Asp Tyr Ser Trp Tyr Ala Leu Asp Tyr Trp Gly Gln Gly Thr
            100                 105                 110

Ser Val Thr Val Ser Ser
            115
```